United States Patent
Grier et al.

(10) Patent No.: US 8,791,985 B2
(45) Date of Patent: Jul. 29, 2014

(54) TRACKING AND CHARACTERIZING PARTICLES WITH HOLOGRAPHIC VIDEO MICROSCOPY

(75) Inventors: David G. Grier, New York, NY (US); Sang-Hyuk Lee, Albany, CA (US); Fook C. Cheong, New York, NY (US)

(73) Assignee: New York University, New York, NY (US)

( * ) Notice: Subject to any disclaimer, the term of this patent is extended or adjusted under 35 U.S.C. 154(b) by 744 days.

(21) Appl. No.: 12/740,628

(22) PCT Filed: Oct. 30, 2008

(86) PCT No.: PCT/US2008/081794
§ 371 (c)(1),
(2), (4) Date: Nov. 12, 2010

(87) PCT Pub. No.: WO2009/059008
PCT Pub. Date: May 7, 2009

(65) Prior Publication Data
US 2011/0043607 A1 Feb. 24, 2011

Related U.S. Application Data

(60) Provisional application No. 61/001,023, filed on Oct. 30, 2007, provisional application No. 61/073,959, filed on Jun. 19, 2008.

(51) Int. Cl.
| | |
|---|---|
| H04N 5/89 | (2006.01) |
| G03H 1/00 | (2006.01) |
| G01P 5/20 | (2006.01) |
| G01P 5/00 | (2006.01) |
| G01N 15/14 | (2006.01) |
| G01N 15/02 | (2006.01) |
| G03H 1/04 | (2006.01) |
| G03H 1/08 | (2006.01) |
| G01N 15/00 | (2006.01) |

(52) U.S. Cl.
CPC ...... *G01N 15/0227* (2013.01); *G01N 2015/025* (2013.01); *G03H 1/0005* (2013.01); *G01P 5/20* (2013.01); *G03H 2001/005* (2013.01); *G03H 2240/56* (2013.01); *G03H 2001/0033* (2013.01); *G03H 2001/0447* (2013.01); *G03H 2001/0825* (2013.01); *G01P 5/001* (2013.01); *G03H 1/0866* (2013.01); *G01N 15/1463* (2013.01); *G01N 2015/0038* (2013.01)
USPC ............... 348/40; 348/79; 356/458; 356/336; 356/512

(58) Field of Classification Search
USPC .......................................................... 348/40
See application file for complete search history.

(56) References Cited

U.S. PATENT DOCUMENTS

| 4,532,422 | A | * | 7/1985 | Nomura et al. ............. 250/306 |
| 4,627,729 | A | * | 12/1986 | Breuckmann et al. ....... 356/458 |

(Continued)

FOREIGN PATENT DOCUMENTS

| CA | 1 159 674 A1 | 1/1984 |
| EP | 0 035 437 | 1/1986 |

(Continued)

OTHER PUBLICATIONS

Author: H. Pin Kao and A. S. Verkman Title:Tracking of Single Fluorescent Particle in the Three Dimensions Date: Sep. 1994 Publisher: Department of Medicine and Physiology Cardiovascular Research Institute and Bioengineering Graduate Group, University of California.*

(Continued)

*Primary Examiner* — Chikaodili E Anyikire
*Assistant Examiner* — Md Haque
(74) *Attorney, Agent, or Firm* — Foley & Lardner LLP

(57) ABSTRACT

In-line holography to create images of a specimen, such as one or more particles dispersed in a transparent medium. Analyzing these images with results from light scattering theory yields the particles' sizes with nanometer resolution, their refractive indexes to within one part in a thousand, and their three dimensional positions with nanometer resolution. This procedure can rapidly and directly characterize mechanical, optical and chemical properties of the specimen and its medium.

23 Claims, 15 Drawing Sheets

(56) References Cited

U.S. PATENT DOCUMENTS

| | | | |
|---|---|---|---|
| 4,740,079 A * | 4/1988 | Koizumi et al. | 356/237.4 |
| 4,986,659 A * | 1/1991 | Bachalo | 356/336 |
| 4,998,788 A * | 3/1991 | Osakabe et al. | 359/1 |
| 5,095,207 A * | 3/1992 | Tong | 850/63 |
| 5,796,498 A | 8/1998 | French | |
| 5,880,841 A * | 3/1999 | Marron et al. | 356/512 |
| 6,097,488 A * | 8/2000 | Grek et al. | 356/364 |
| 6,281,994 B1 * | 8/2001 | Horikoshi et al. | 359/32 |
| 6,710,874 B2 * | 3/2004 | Mavliev | 356/336 |
| 7,248,282 B2 * | 7/2007 | Maddison | 348/79 |
| 8,119,988 B2 | 2/2012 | Daido et al. | |
| 2003/0021382 A1 * | 1/2003 | Iwanczyk et al. | 378/175 |
| 2007/0070303 A1 * | 3/2007 | Yonekubo | 353/94 |

FOREIGN PATENT DOCUMENTS

| | | |
|---|---|---|
| EP | 0 278 714 | 8/1988 |
| JP | 55-096976 A | 7/1980 |
| JP | 3-251888 A | 11/1991 |
| JP | 2001-034148 A | 2/2001 |
| JP | 2005-0512127 A | 4/2005 |
| JP | 2007-279475 A | 10/2007 |
| WO | WO03/048868 A1 | 6/2003 |
| WO | WO 2008/092107 A1 | 7/2008 |
| WO | WO 2008/127410 A2 | 10/2008 |
| WO | WO 2009/059008 A1 | 5/2009 |

OTHER PUBLICATIONS

JP Office Action (English Translation), Application No. 2011-546331, Oct. 25, 2012, 2 pages.

JP Preliminary Report of Issuance of Office Action, Application No. 2010-531335, Oct. 23, 2012, 4 pages.

Colomb, et al., "Polarization microscopy by use of digital holography: application to optical-fiber birefringence measurements", *Applied Optics*, Jul. 20, 2005, pp. 4461-4469, vol. 44, No. 21, Optical Society of America.

Lee, et al., "Characterizing and tracking single colloidal particles with video holographic microscopy", *Optics Express*, Dec. 24, 2007, pp. 18275-18282, vol. 15, No. 26, Optical Society of America.

Rappaz et al., "Simultaneous cell morphometry and refractive index measurement with dual-wavelength digital holographic microscopy and dye-enhanced dispersion of perfusion medium", *Optics Letters*, Apr. 1, 2008, pp. 744-746, vol. 33, No. 7, Optical Society of America.

Rappaz et al., "Erythrocytes volume and refractive index measurement with a Digital Hololgraphic Microscope", *Proc. Of SPIE*, (2007), pp. 644509-1-644509-5, vol. 6445, Optical Diagnostics and Sensing VII.

Lee, Sang-Hyuk et al., "Holographic Microscopy of Holographically Trapped Three-Dimensional Structures", *Optics Express*, (2007) pp. 1505-1512, Optical Society of America.

International Search Report dated Apr. 30, 2010 for PCT/US2010/021045, 2 pages.

International Search Report dated Feb. 12, 2009 for PCT/US2008/081794, 1 page.

Denis et al., "Direct Extraction of the Mean Particle Size from a Digital Hologram", *Applied Optics*, Feb. 10, 2006, pp. 944-952, vol. 45, No. 5, Optical Society of America.

Moreno et al., "Particle Positioning from Charge-Coupled Device Images by the Generalized Lorenz-Mie Theory and Comparison with Experiment", *Applied Optics*, Oct. 1, 2000, pp. 5117-5124, vol. 39, No. 28, Optical Society of America.

Sheng et al., "Digital Holographic Microscope for Measuring Three-Dimensional Particle distributions and Motions", *Applied Optics*, Jun. 1, 2006, pp. 3893-3901, vol. 45, No. 16, Optical Society of America.

First Office Action with English Translation in Chinese Application No. 20108009712.X, dated Dec. 18, 2012, 21 pages.

Japanese Office Action with English Translation dated Dec. 18, 2013, Japanese Application No. 201080009712.X, 21 pages.

Chinese Office Action dated Jul. 18, 2013, 24 pages.

Sciammarella, Cesar A., Measurement of Mechanical Properties of Materials in the Micrometer Range Using Electronic Holographic Moiré, Optical Engineering, vol. 42, Issue 5, pp. 1215-1222, May 2003.

\* cited by examiner

IMAGING PLANE

MEASURED
HOLOGRAM

FIT

● ● ● x   ■ ■ ■ y   ◆ ◆ ◆ z

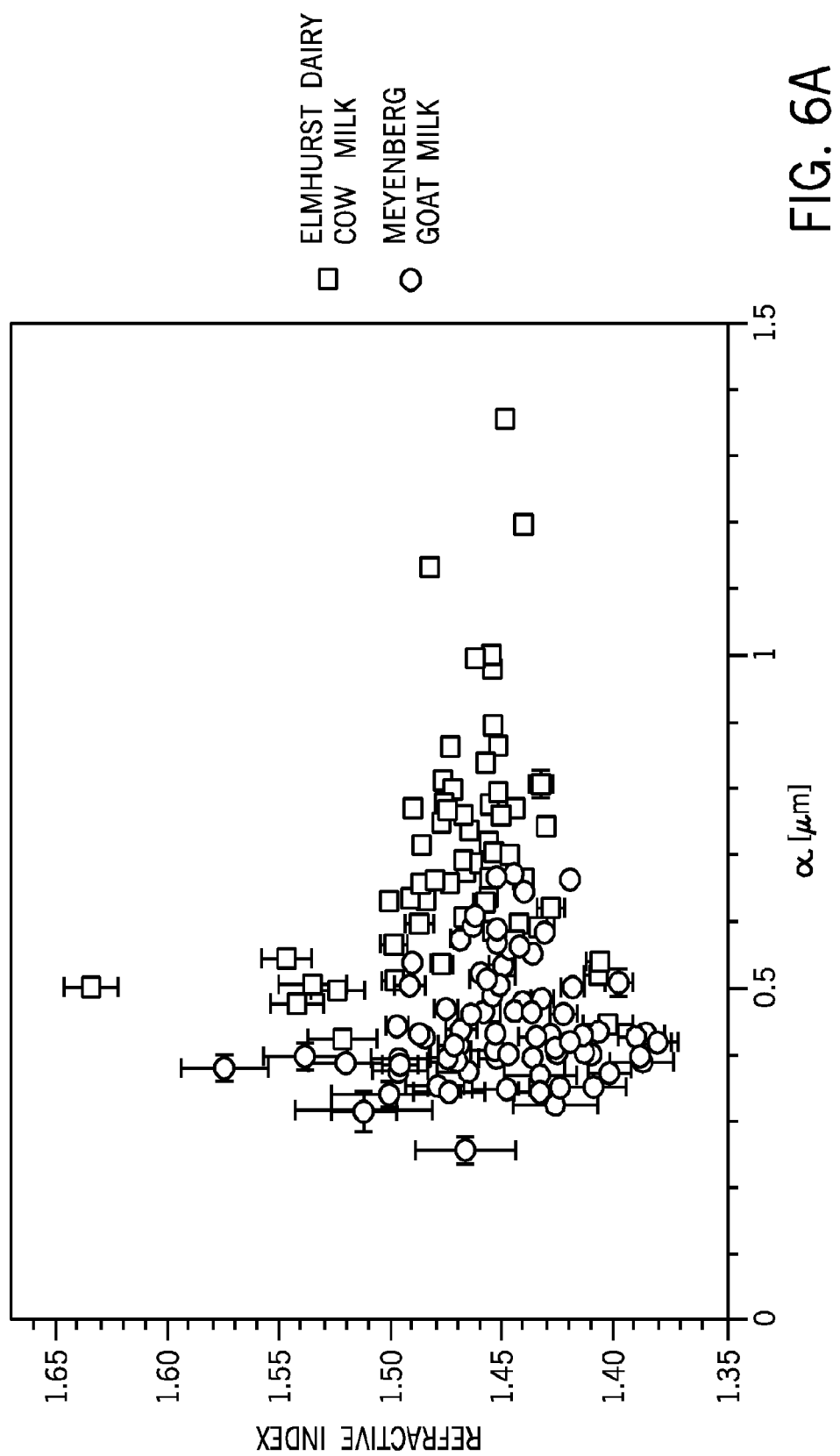

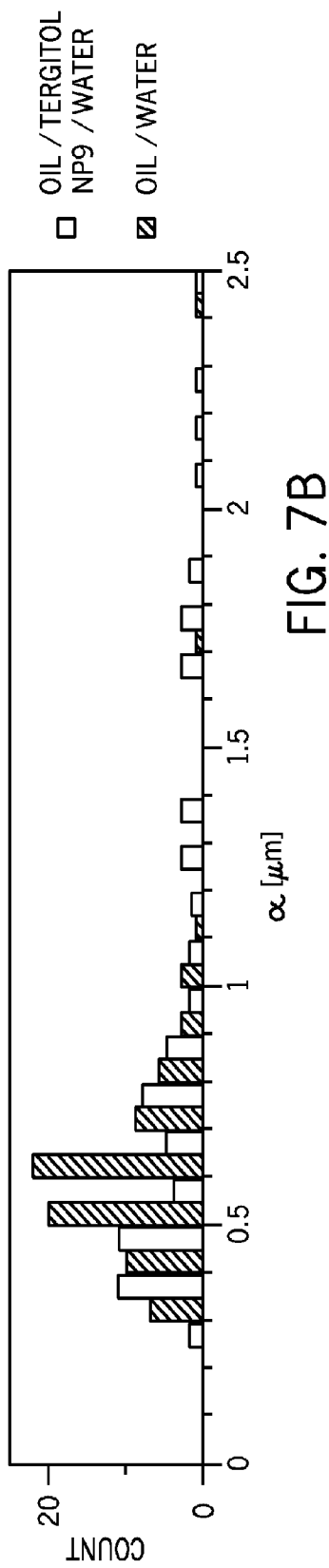
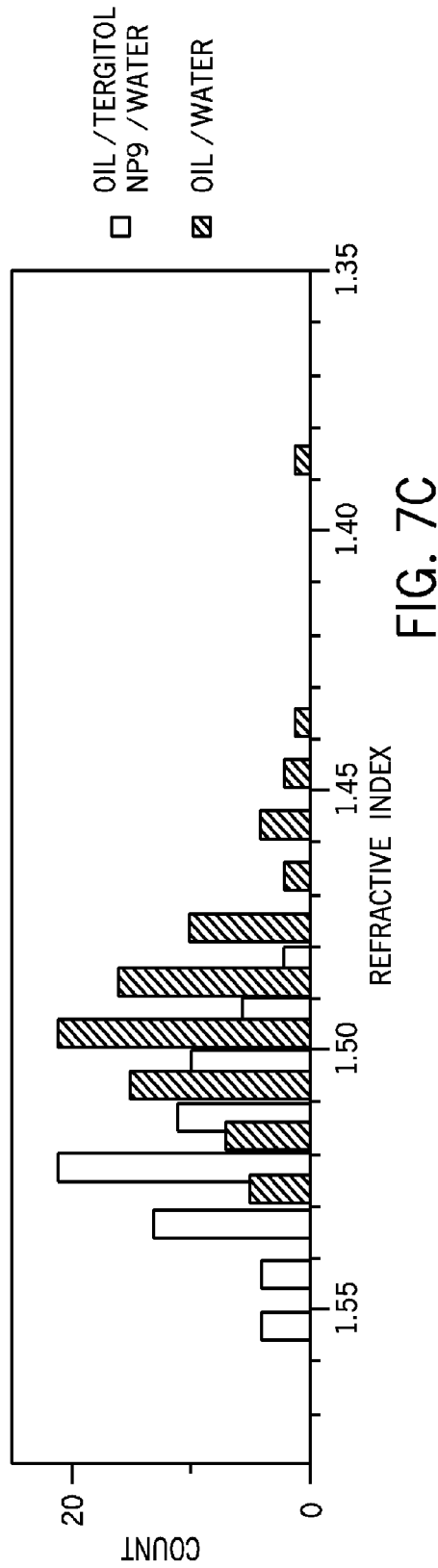
FIG. 7B
FIG. 7C

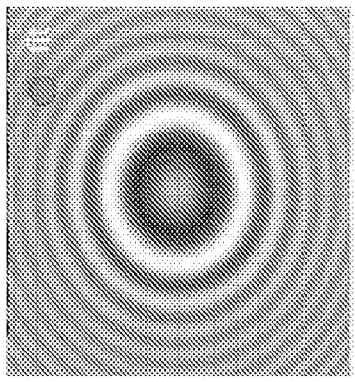
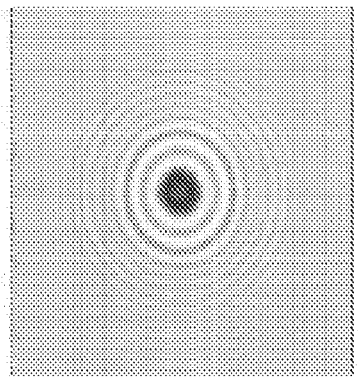
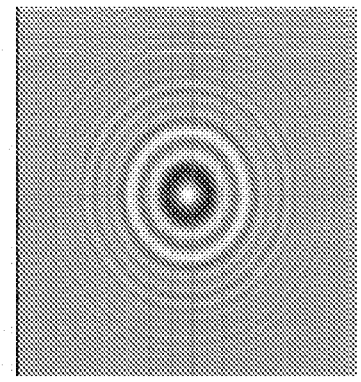
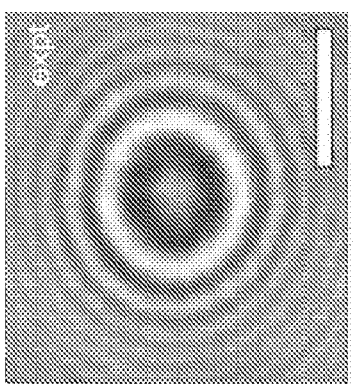
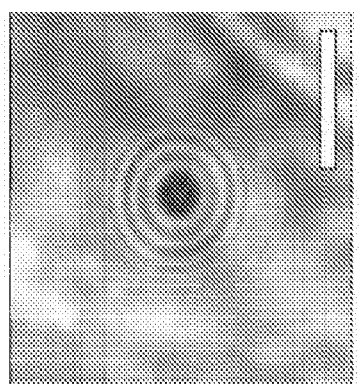
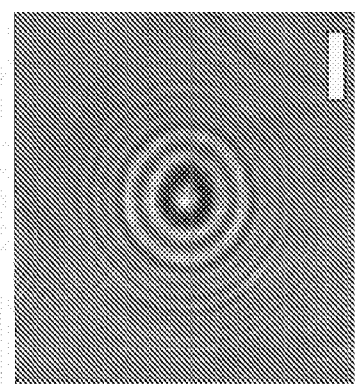
FIG. 8A(2)　FIG. 8B(2)　FIG. 8C(2)
FIG. 8A(1)　FIG. 8B(1)　FIG. 8C(1)

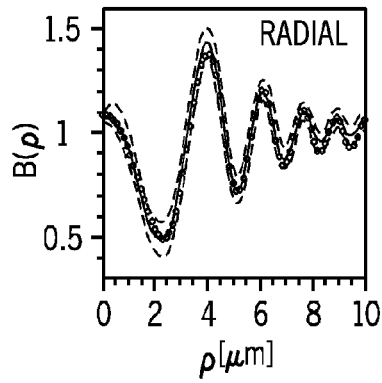
FIG. 8A(3)
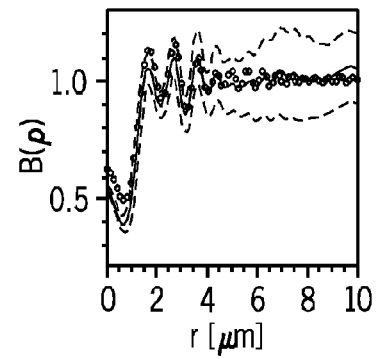
FIG. 8B(3)
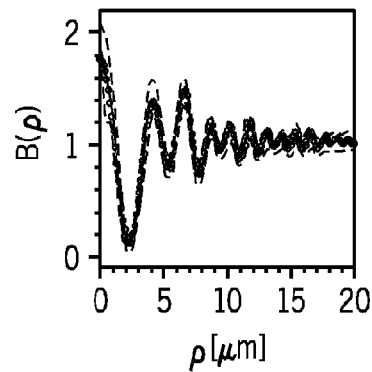
FIG. 8C(3)
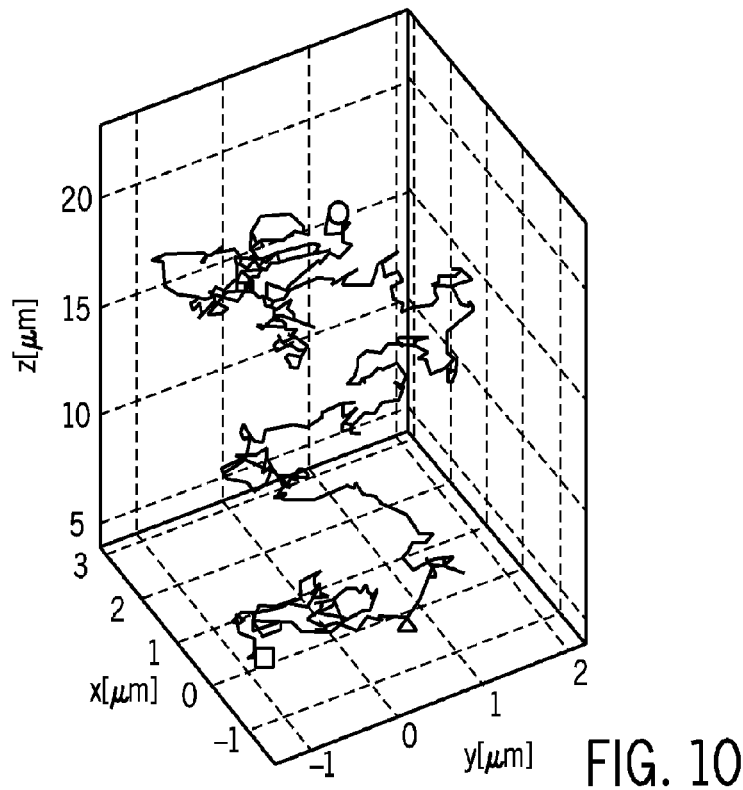
FIG. 10

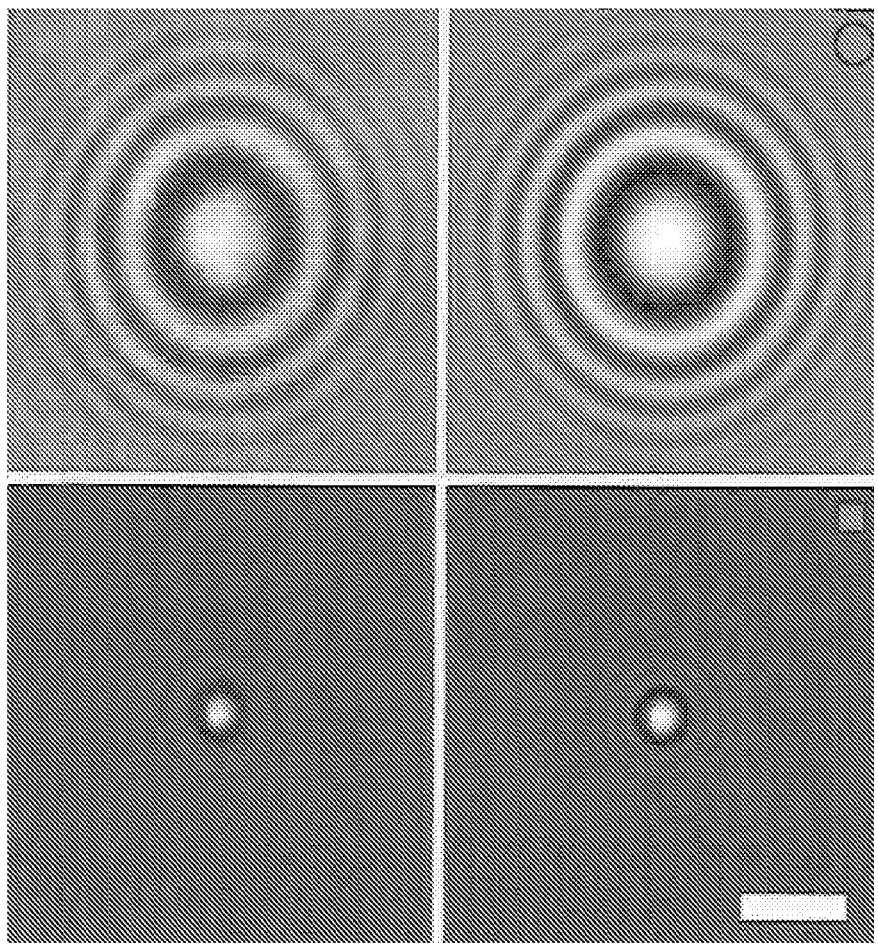

TRACKING AND CHARACTERIZING PARTICLES WITH HOLOGRAPHIC VIDEO MICROSCOPY

CROSS-REFERENCE TO RELATED PATENT APPLICATIONS

This application claims the benefit under 35 USC 119(e) of U.S. Application 61/001,023, filed Oct. 30, 2007 and U.S. Application 61/073,959, filed Jun. 19, 2008, incorporated herein by reference in its entirety.

This work was supported by the National Science Foundation under Grant Number DMR-0606415.

BACKGROUND OF THE INVENTION

The present system and method are directed to measuring the three-dimensional position of colloidal particles within colloidal dispersions, and furthermore to characterizing each particle's shape, size, and optical properties, by quantitative analysis of holograms recorded through holographic video microscopy. Information obtained from this analysis can be used to characterize the colloidal particles themselves. This information also can be used to measure and assay the properties of the medium within which the particles are dispersed. In all such applications, quantitative holographic video microscopy offers substantial advantages over methods and analysis systems that have been previously described and practiced.

Particle-image velocimetry is widely applied for measuring the trajectories of colloidal particles dispersed in transparent media. Conventional implementations of particle-imaging velocimetry involve forming images of the particles using standard light microscopy and then analyzing those images through methods of computer image analysis. Such measurements and analyses typically provide information on individual particles' positions in the microscope's focal plane, but not on the particles' axial displacements relative to the focal plane. In cases where axial tracking information is extracted, the results typically have substantially poorer spatial resolution than the in-plane positions. Measurements of axial positions, furthermore, require separate calibration measurements for each particle. Such conventional particle-imaging methods generally provide little information on the particles' sizes, shapes, or compositions. The range of axial displacements over which conventional particle-imaging methods can be applied is limited by the depth of focus of the microscope because images of particles that move too far from the focal plane become too dim and diffuse to analyze.

Applications of image-based particle tracking include measuring streamlines in flowing fluids, assessing the thermodynamic stability of colloidal dispersions against aggregation and flocculation, measuring interactions among colloidal particles, measuring colloidal particles' interactions with surfaces, assessing particles' responses to external fields and forces, characterizing the particles' viscous drag characteristics, and using the particles' motions as probes of the viscoelastic and rheological properties of the embedding medium. The latter class of measurements, in which colloidal particles are used as microscopic probes of the medium's rheology, is commonly termed particle-tracking microrheology. All such applications benefit from particle-tracking techniques that offer better spatial resolution, three-dimensional tracking, and a wider axial range. Some of these applications, such as microrheology, also require information on the probe particles' characteristics, such as their radii. Typically, such particle characterization data are obtained in separate measurements.

In the particular case of microrheology, other methods are available for acquiring equivalent information on a medium's viscoelastic properties. Among these are diffusing wave spectroscopy, dynamic light scattering and interferometric particle tracking. All such methods offer superior bandwidth to those based on particle imaging. The first two do not, however, offer spatially resolved measurements, which are necessary in some applications. Interferometric particle tracking offers both excellent bandwidth and excellent tracking resolution. It can only be applied to one or two points in a sample, however, and so cannot be used for multi-point assays of rheological properties. None of these methods is suitable for analyzing the properties of inhomogeneous samples.

Individual colloidal particles typically are characterized by their shape, their size, their bulk composition, and their surface properties. Colloidal dispersions are characterized by the distributions of these quantities as well as by the overall concentration of particles. Size and shape can be assessed through electron microscopy on dried and otherwise prepared samples. Preparation can change the particles' properties, however, so that the results of such measurements might not accurately reflect the particles' characteristics in situ. Light scattering methods generally are used for in situ analysis of colloidal particles' sizes. Such measurements, however, provide a sample-averaged view of the particles in a dispersion, and generally require careful interpretation with approximate or phenomenological models for the particles' size distribution, shapes, and refractive indexes. Commonly used commercial particle sizing instruments are based on these methods and share their limitations. These methods, furthermore, cannot be used to characterize the particular particles used in particle-tracking measurements. Other particle-sizing instruments, such as Coulter counters, similarly rely on indirect methods to measure particle sizes and cannot be applied in situ. A variety of methods also are known from measuring colloidal particles' refractive indexes. Conventional light scattering methods generally provide sample-averaged values for the refractive index and require information on the particles' sizes and shapes. A particularly effective method involves matching the refractive index of a fluid to that of the particles and then measuring the refractive index of the fluid. This method requires index-matching fluids that are compatible with the colloids and is highly limited in the range of refractive indexes that can be assessed.

SUMMARY OF THE INVENTION

Quantitative analysis of images obtained through holographic video microscopy provides the information required to simultaneously track and characterize large numbers of colloidal particles, and yields information on each particle individually. For tracking particles, this method offers nanometer-scale position measurements in three dimensions over an exceedingly large range of axial positions. Such high-resolution wide-range three-dimensional tracking data is ideal for applications in microrheology, and similarly can be used beneficially in any application where conventional particle tracking currently is applied. Holographic particle tracking works for particles ranging in size from a few nanometers up to at least a few micrometers. It offers the full time resolution of the video camera used to acquire the holograms. For particle characterization, holographic analysis yields the radius with nanometer resolution and the complex refractive index with a relative error no worse than one part in a thousand. It covers the full range of refractive indexes from low-index bubbles in high-index media to particles whose refractive indexes are too high to be assessed by other means. These specifications surpass those of many methods devoted to particle characterization alone. The combination of high-resolution particle tracking with precise in situ particle characterization makes possible measurements that cannot be performed by other means.

Various aspects of the invention are described herein; and these and other improvements are described in greater detail hereinbelow, including the drawings described hereinafter.

BRIEF DESCRIPTION OF THE DRAWINGS

FIG. 6A illustrates fat globule radius versus refractive index for commercial milk samples, each data point representing results for a single fat droplet (error bars are computed from the normalized variance index of fitting parameters)

FIG. 7B shows count distribution versus diameter and FIG. 7C shows count distribution versus refractive index;

FIG. 8A(1) shows a normalized hologram $B(\rho)$ from a polystyrene sphere of 1.43 µm diameter in water at $z_p=22.7$ µm; FIG. 8A(2) is a numerical fit using Eq. (18); FIG. 8A(3) shows the azimuthally averaged radial profile $B(\rho)$ for the sphere; FIG. 8B(1) shows hologram data for a 1.45 µm diameter $TiO_2$ sphere dispersed in immersion oil ($n_m=1.515$) at $z_p=7.0$ µm; FIG. 8B(2) shows the numerical fit as in the method of FIG. 8A(3); FIG. 8B(3) shows the corresponding azimuthally averaged radial profile $B(\rho)$; FIG. 8C(1) shows hologram data for a 4.5 µm $SiO_2$ sphere in water at $z_p=38.8$ µm; FIG. 8C(2) shows the numerical fit as in the method of FIG. 8A(3) and FIG. 8C(3) shows the corresponding azimuthally averaged radial profile $B(\rho)$;

FIG. 9A(1) shows digital hologram images of a colloidal silica sphere at the beginning of a trajectory; FIG. 9A(2) shows the colloidal silica sphere at the end of the trajectory; FIG. 9B(1) shows the corresponding numerical fit using Eq. (18) at the beginning of the trajectory and FIG. 9B(2) the corresponding fit at the end of the trajectory;

FIG. 10 illustrates a 3-D trajectory of the colloidal silica sphere showing its starting point (a circle) and end point (square) labeled;

DETAILED DESCRIPTION OF PREFERRED EMBODIMENTS

Figure 1A:
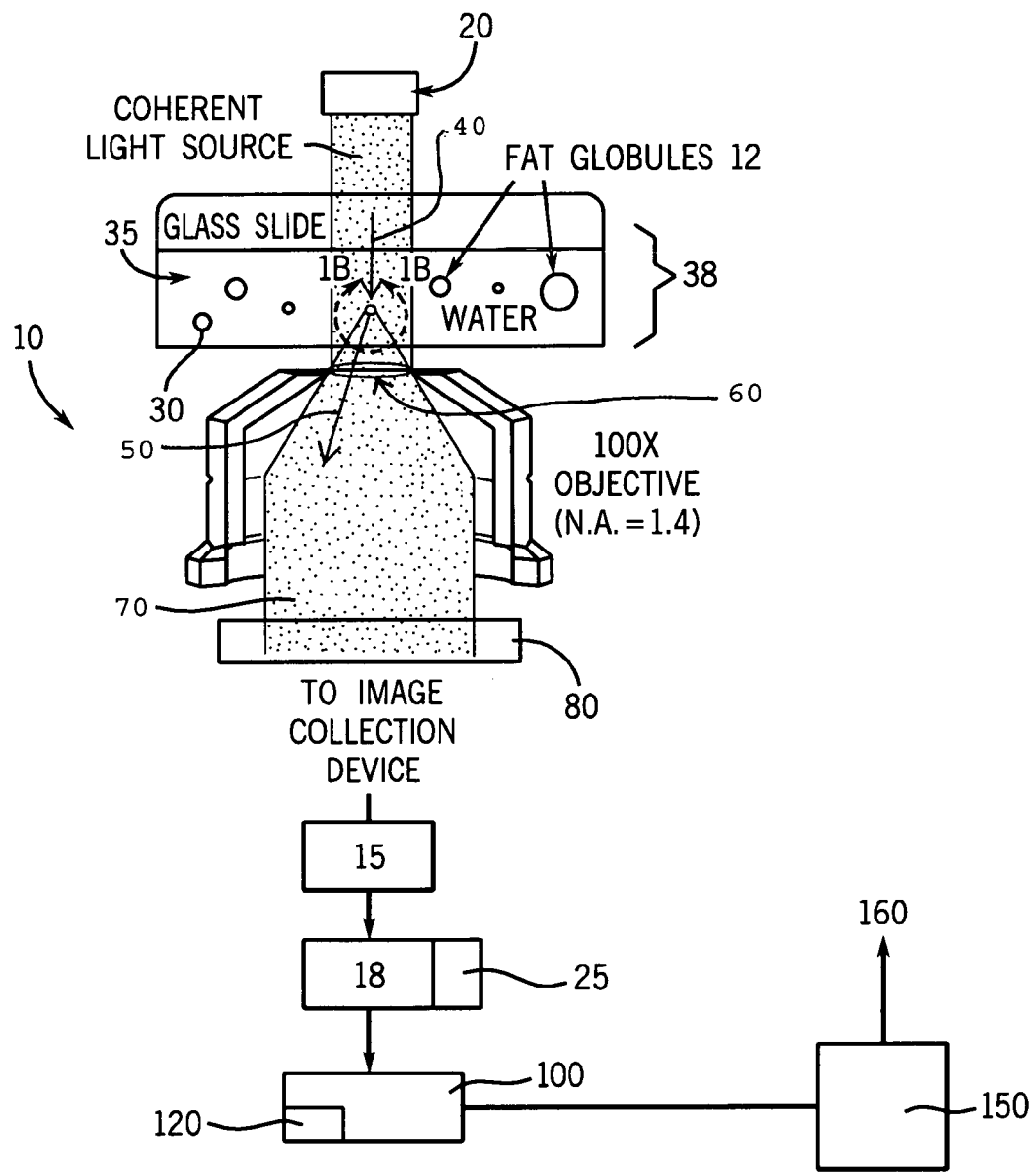
FIG. 1A illustrates a schematic representation of a holographic video microscope.

The subject holographic microscope 10, depicted schematically in FIG. 1A, is based on a commercial inverted light microscope (Zeiss Axiovert TV 100 S). A conventional incandescent illuminator is replaced with a collimated 10 mW HeNe laser 20 (for example, Uniphase) operating a vacuum wavelength of $\lambda=632.8$ nm. A specimen, such as an individual particle 12 or different phase 30 within a medium 35 disposed on a specimen stage or holder 38 at position $r_p$ scatters a small portion of the plane-wave illumination light 40. Scattered light 50 then propagates to the focal plane 60 of the microscope 10, where the light 50 interferes with the unscattered portion of the laser beam light 40. The resulting interference pattern is magnified by the microscope's objective lens 70 (such as, an S Plan Apo, 100x, NA 1.4, oil immersion) and projected by a video eyepiece 80 (0.63x) onto a CCD camera 15 (such as, NEC TI-324AII) before being recorded as uncompressed digital video with a digital video recorder 18 (for example, Panasonic DVR-H110, not shown) and accumulated data is processed by a computer 100 executing various computer software embedded in module 120; and the computer 100 can include a non-transitory computer readable medium. In a preferred form the invention the computer software on the module 120 includes a set of instructions for operating on data characteristic of the specimen. The data characteristic of the specimen 12, 30 relates to an interference pattern arising from interaction of the laser light 50 scattered from the specimen 12, 30 and an unscattered portion of the laser light 40. The set of instructions further include a scattering function which upon execution provides a convergent solution descriptive of properties of the specimen 12, 30, thereby enabling characterization of at least one of a mechanical property, an optical property, and a chemical property of the specimen 12, 30.

Each holographic image in the video stream provided by the recorder 18 is a time-resolved snapshot of the three-dimensional distribution of scatterers in the microscope's field of view. In additional embodiments a plurality of time snapshots allow tracking particle trajectory and obtaining characteristic properties. We then use results of the Lorenz-Mie theory of light scattering (or other appropriate light scattering methodologies embedded as a program in the software module 120) by the small particles 12 to measure characteristics of each particle 12 or the different phase 30. In the system of FIG. 1A, the specimen data output from the recorder 18 and processed by the computer 100 can be output to a control system 150 for generating quality control or manufacturing control signals 100 for the specimen 12, 30.

Figure 2A:
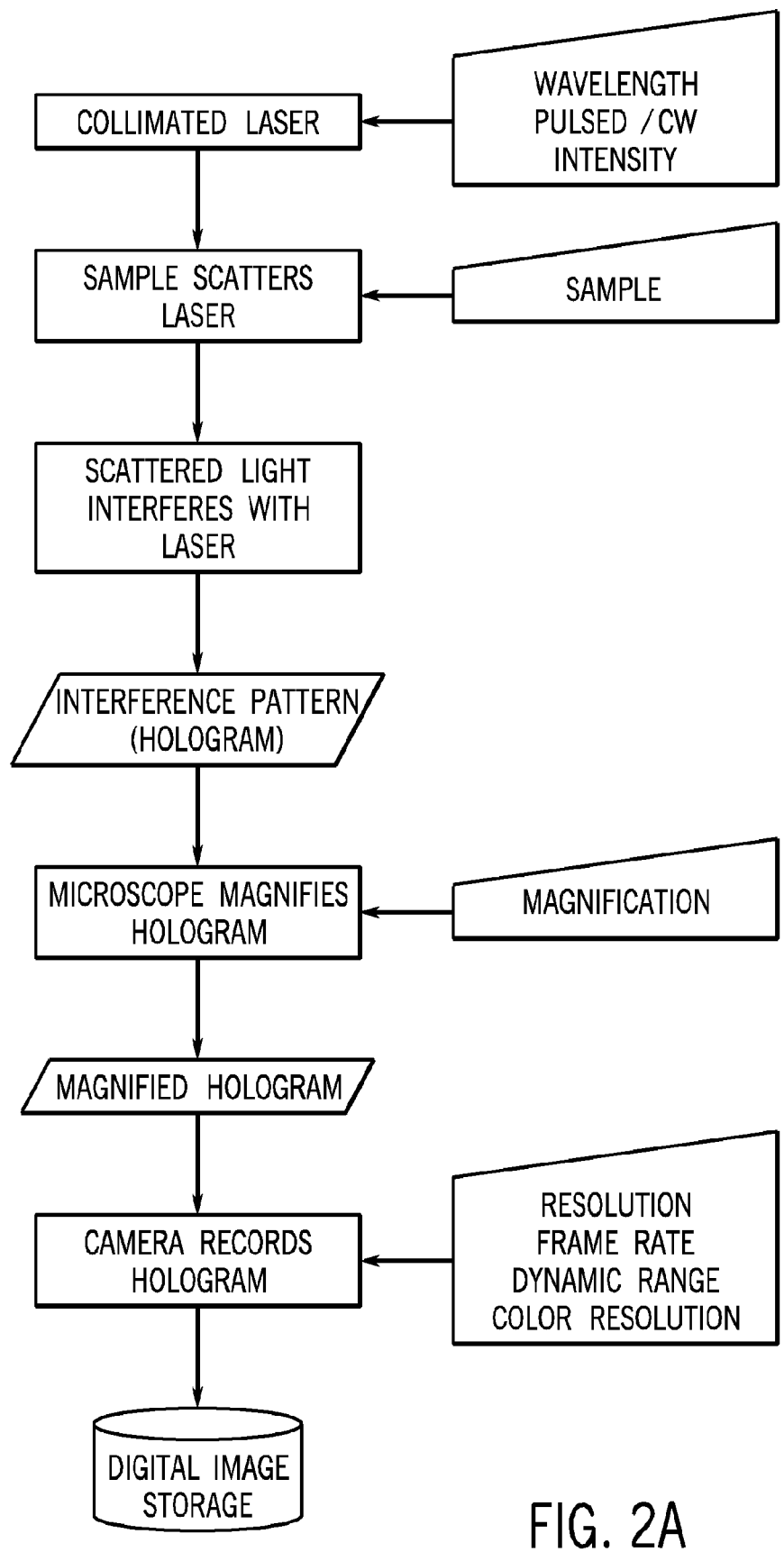
FIG. 2A illustrates a schematic flow diagram of a preferred embodiment of analyzing a specimen to provide characteristic property information.
Figure 2B:
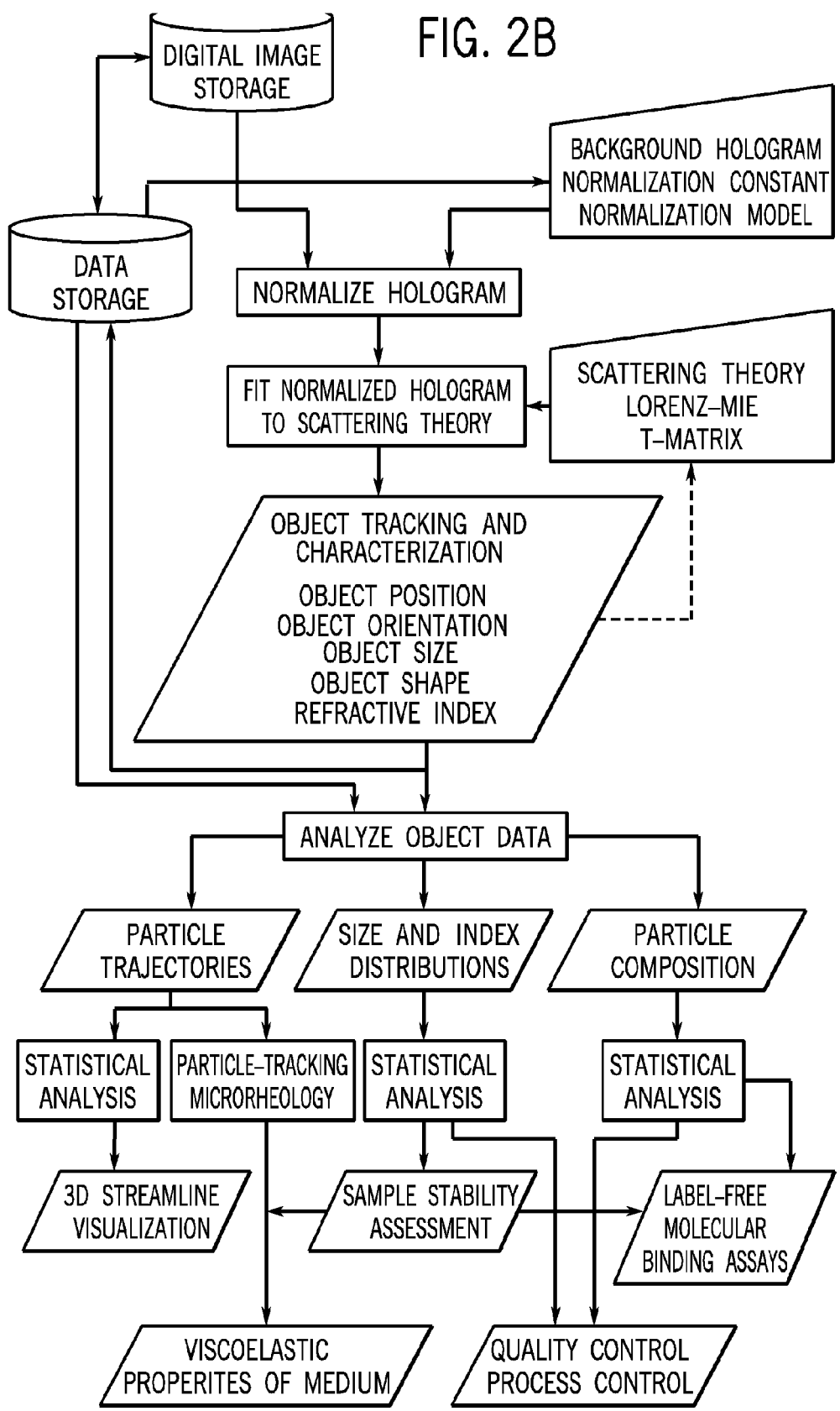
FIG. 2B shows details of a computer software driven methodology of processing the specimen data.

In a most preferred embodiment the microscope 10 is operated in accordance with the flow diagram shown in FIGS. 2A and 2B. Acquisition of holographic images begins with the choice of the laser 20 used to illuminate the specimen 12, 30. Characteristics of the laser 20 that may be selected for a particular application include the wavelength of the light 40, the number of distinct wavelengths of the light 40, the coherence length, the intensity of the light 40 at each wavelength, and whether the laser 20 is continuous or pulsed. If the laser 20 is pulsed, the shape and timing of the pulses may be optimized for different application. These choices typically would be made in consideration of the intended application and of the other hardware and software components in the microscope 10. For example, a pulsed form of the laser 20 might be preferable for time-resolved imaging of rapidly moving objects. The pulses might then be synchronized with the shutter of the video recorder 18 or other camera used to record images. The wavelength similarly might be selected to take advantage of optical properties of the specimen 12, 30. A plurality of wavelengths of the laser 20 might be selected to acquire spectroscopic information through analysis of holograms recorded in different wavelengths. Holograms at different wavelengths might be recorded simultaneously with a camera (such as the video recorder 18) capable of recording color information. They might be recorded with multiple cameras, each selected for a particular wavelength. Or, they might be recorded sequentially with one or more cameras.

For in-line holography, the specimen 12, 30 is most preferably sufficiently transparent for a sufficient fraction of the illuminating laser 20 to pass through undistorted so as to form an interference pattern. The specimen 12, 30 thus has to be mounted in a transparent form of the sample holder 38; and the sample holder 38 mounted rigidly in the laser beam 20, disposed so that the resulting interference pattern is visible to the microscope 10. If these conditions are met, the light 40 scattered by the specimen 12, 30 to provide the light 50 which will interfere with the unscattered portion of the laser beam 20 to form an interference pattern, or hologram. The role of the microscope 10 is to magnify the hologram and project the magnified hologram onto the camera 18. The microscope's objective lens 70 and eyepiece 80 thus is preferably selected to optimize collection, magnification and projection of the light 40, at the wavelength of choice.

The video recorder or camera 18, perhaps coupled with a separate digitization system, records the hologram, digitizes it, and transfers the digitized image to a digital image storage system (shown, for example, as 25 in FIG. 1A). The camera's pixel count, spatial resolution and frame rate establishes the spatial range, spatial resolution and temporal bandwidth of measurements that can be performed with holographic microscopy methods. In addition, its dynamic range establishes the intensity of the laser 20 required to acquire useful images and the amount of information that can be acquired from each image. Its ability to record color information determines what role the camera 18 can play in acquiring holograms at multiple wavelengths. Images acquired by the camera 18 can be recorded for later analysis, or transferred directly to image analysis routines for real-time analysis.

The images can be prepared for analysis and subsequent use in the manner shown in FIG. 2B. Images acquired by the camera 18 and, perhaps, data stored in the digital image storage system 25, consist of arrays of pixels, each of which records the local intensity value as a number. Before these numbers can be analyzed with light scattering theory, they are most preferably appropriately normalized. Normalization may consist of dividing the image by a previously recorded background image, as described herein. This has the benefit of eliminating intensity variations in the image due to spurious interference fringes. Alternatively, it may consist of dividing the entire image by a normalization constant, or normalizing the image by a numerical model for a background illumination pattern.

Once the image is normalized, it can be analyzed by fitting to predictions based on selected appropriate light scattering theory. Light scattering theory comprises several different mathematical formulations, including Lorenz-Mie theory, T-matrix theory, and other approaches to predicting the electric and magnetic waves scattered by an illuminated object. Any such formulation may be used to analyze a normalized image. In the particular case that the specimen 12, 30 is a sphere, Lorenz-Mie theory is particularly well suited. For more complex structures, T-matrix theory may be preferable.

Once the appropriate formulation for the scattered light field has been selected, the normalized image may be fit to the theory by manipulating the adjustable parameters. In the particular case of a homogeneous isotropic spherical object for the specimen 12, 30, the adjustable parameters include the sphere's three-dimensional position, its radius, and its complex refractive index. In the case of more complex objects, additional fitting parameters may be required. In general, the necessary fit involves a highly nonlinear optimization of the adjustable parameters. In our reduction to practice of this method, we adopted the Levenberg-Marquardt nonlinear least-squares optimization algorithm. Other algorithms may be preferable for some applications. The fits may be performed on a pixel-by-pixel basis using the CPU of the computer 100. Alternatively, the computations may be accelerated though the use of a graphics processing unit (GPU), or another such parallel-processing system (also represented as "computer 100" in FIG. 1A).

Fits may be performed for the specimen 12, 30 in each recorded holographic image. Alternatively, some particular specimen 12, 30 may be selected in each image for further consideration. Once an image has been analyzed, the object data may be analyzed either in isolation or in conjunction with data from other images. The object data may be the desired final product for use thereof. This could be the case for verifying a three-dimensional configuration of the specimen 12, 30, or assessing the optical characteristics of a sample of the specimen 12, 30.

A sequence of holographic images of an individual one of the specimen 12, 30 may be combined to develop a time-resolved measurement of that specimen's three-dimensional trajectory. Such trajectories themselves may be used as inputs for further analysis. For example, statistical analysis of trajectory data may be used to develop measurements of the velocity field in a flowing fluid. Such measurements are conventionally known by the term particle-image velocimetry. The variation based on holographic particle tracking might therefore be termed holographic particle-image velocimetry. Alternatively, trajectory data may be analyzed to obtain information about the viscoelastic properties of the medium 35 within which a plurality of the specimen particles 18 is dispersed, which can be termed as holographic microrheology (this will be described in more detail hereinafter in Section A).

As described in more detail hereinafter the specimen's size and refractive index data and an individual particle's size and refractive index may be monitored over time. These values should remain constant in a stable system. Variations in these values provide information about the changing conditions within the system. Such information may be useful in such applications as holographic microrheology. Alternatively, the size and refractive index of a statistical ensemble of the particles 18 or the phase 30 may be obtained from a plurality of holographic images. Such ensembles may be analyzed to estimate the statistical distribution of sizes and refractive indexes within a bulk specimen 12, 30. Such information is useful in monitoring processes and products for quality and consistency. In the case of non-spherical specimens 12, 30, additional information such as shape and orientation also may be obtained, and statistical analyses performed.

In some cases, the chemical composition of the specimen 12, 30 may be assessed by measuring its refractive index at a plurality of wavelengths. In the case of heterogeneous specimen such as coated spheres, composition analysis can detect the presence or composition of coatings on the surface of the specimen 12, 30. Composition analysis is useful for process control and product quality assurance, for instance as a means of detecting adulterants in emulsions or particle-based products. Detection of molecular scale coatings is useful for label-free molecular binding assays. Other applications of the geometric and compositional data also should be apparent, including applications that also make use of tracking data.

A. Microrheology of a Medium

In various embodiments, this methodology was applied to analysis of numerous different types of the particles and phases 12, 30. In one preferred embodiment we have performed holographic microrheological analyses of a medium's viscoelastic properties by analyzing its thermally-driven fluctuations, either directly, or through their influence on embedded probe particles. In one embodiment the approach can monitor a probe particle's mean-square positional fluctuations, $\langle \Delta r^2(t) \rangle$, and uses a generalized Stokes-Einstein relation to extract the medium's frequency-dependent storage modulus, $G'(\omega)$. This is related by the Kramer-Kronig relation to the frequency-dependent loss modulus, $G''(\omega)$, which completes the micromechanical description.

Our example probe particles are charge-stabilized polystyrene spheres of nominal radius a=0.75 μm (Duke Scientific, Catalog #5153A, Lot #26621) that are dispersed at random into a sample medium by vortexing. The sample medium then is charged into a transparent container formed by bonding a no. 1 glass cover slip to the face of a microscope slide. The sealed sample medium is allowed to come to thermal and mechanical equilibrium on the microscope stage at T=23±1° C.

Holographic images are recorded as an uncompressed digital video stream at 30 frames per second on a digital video recorder (Panasonic DMR-E100H). Each image then is analyzed to measure the probe particle's three-dimensional location relative to the center of the microscope's focal plane.

More specifically, the collimated laser illuminates the probe particle at position $r_p$ with a plane-wave incident electric field, $E_0(r_p)=u_0(r)\exp(-ikz_p)$, where $k=2\pi n_m/\lambda$ is the wavenumber of the light in a medium of refractive index $n_m$. The field scattered by the particle, $E_s(r)=u_0(r_p)f_m(r-r_p)$, propagates to the focal plane at z=0, where it interferes with the incident beam. The distribution of scattered light is described by the conventional Lorenz-Mie scattering function, $f_m(r-r_p)$, which depends on the particle's position $r_p$, its radius, a, and its refractive index, $n_p$.

Figure 1B:
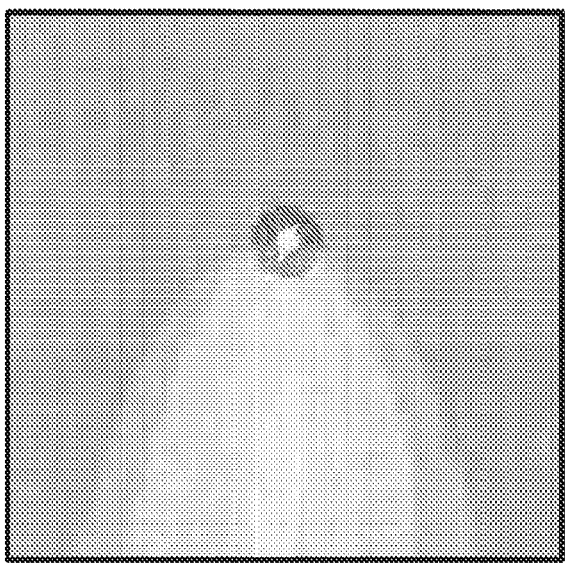
FIG. 1B shows the resulting light scattering in an imaging plane depicted in FIG. 1A.
Figure 1C:
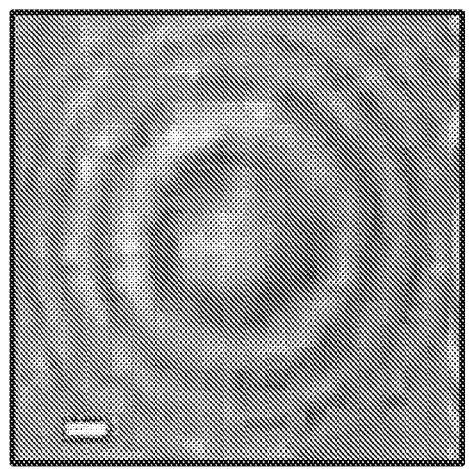
FIG. 1C illustrates a resulting measured hologram and FIG. 1D shows a fitted hologram using a method of the invention.
Figure 1D:
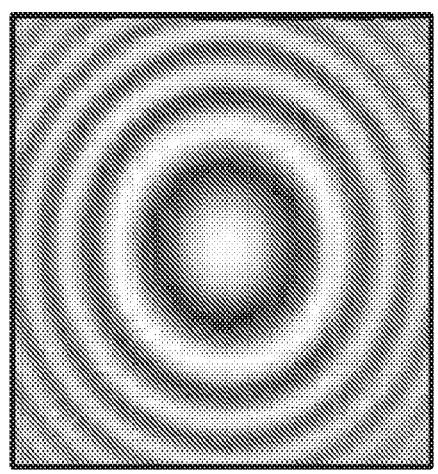

In practice, the incident illumination varies with position, so that we normalize the measured interference pattern, I(r), by a measurement of the incident illumination $I_0(r)=|u_0(r)|^2$ to obtain, $$\frac{I(r)}{I_0(r)} = 1 + 2\alpha \mathcal{R}\{f_s(r-r_p) \cdot \hat{\varepsilon} e^{-ikz_p}\} + \alpha^2 |f_s(r-r_p)|^2, \quad (1)$$

where α≈1 accounts for variations in $I_0(r_p)$. Equation (1) can be fit to normalized images such as the example shown in FIG. 1B, with the particle's position, radius, and refractive index as free parameters. Whereas conventional bright-field particle tracking on the same instrument offers 10 nm in-plane resolution and 100 nm axial resolution, holographic particle tracking performs at least one order of magnitude better. Unlike conventional particle tracking, moreover, holographic tracking does not require separate calibrations for axial measurements.

We can assess the measurement error in the particles' positions by tracking probe particles freely diffusing in Newtonian fluids such as water. Provided the particle is far enough from bounding surfaces, its mean-square displacement in each of the three Cartesian directions should evolve according to the Stokes-Einstein relation $$\langle \Delta r_j^2(t) \rangle = \langle |r_j(t+\tau)-r_j(\tau)|^2 \rangle = 2D_0 t, \quad (2)$$

Where $D_0=k_B T/(6\pi\eta a)$ is the diffusion coefficient for a sphere in a fluid of viscosity η at absolute temperature T. The angle brackets in Eq. (2) denote an ensemble average over starting times. Restricting the average to starting times that are separated by the interval t ensures that contributions to $\langle \Delta r_j^2(t) \rangle$ are statistically independent. When analyzing a single discretely sampled trajectory, however, this choice yields disproportionately large statistical errors at longer lag times, t. Averaging over all starting times improves the estimate for $\langle \Delta r_j^2(t) \rangle$ and is justified if the trajectory may be treated as a Markov process. This is the case for the thermally driven trajectories we consider, and such exhaustive sampling enables us to estimate the mean-squared displacement from a single trajectory measured over a few thousand time steps. Statistical errors in $\langle \Delta r_j^2(t) \rangle$ must be corrected for covariances among correlated measurements over the interval t.

Measurements of $r_j(t)$ also suffer from random errors whose mean value, $\epsilon_j$, establishes the tracking resolution. These errors increase the particle's apparent mean-square displacement by $2\epsilon_j^2$, independent of t. A complementary error due to motional blurring during the camera's shutter period, $\tau_s$, reduces the apparent mean-square displacement. The result is given by, $$\langle \Delta r_j^2(t) \rangle = 2D_0^{t+2}\left(\varepsilon_j^2 - \frac{1}{3}D_0\tau_s\right) \quad (3)$$

accounts for both effects, and enables us to measure $\epsilon_j$.

The Fourier transform of $\langle \Delta r_j^2(t) \rangle$ is related to the complex frequency-dependent viscoelastic modulus through the phenomenological generalized Stokes-Einstein relation, $$G^*(\omega) = -i\frac{k_B T}{\pi a \omega \langle \Delta \hat{r}_j^2(\omega) \rangle} \quad (4)$$

$$\approx i^{\alpha j(\omega)}\frac{k_B T}{\pi a \langle \Delta r_j^2(1/\omega) \rangle \Gamma(1+\alpha_j(\omega))} \quad (5)$$

where $\Gamma(x)$ is the gamma function and, $$\alpha_j(\omega) = \frac{d \ln\langle\Delta r_j^2(t)\rangle}{d \ln t}\bigg|_{t=\frac{1}{\omega}} \quad (6)$$

From this, we obtain $$G'(\omega)=\Re\{G(\omega)\} \text{ and } G''(\omega)=\Im\{G(\omega)\}. \quad (7)$$

$G'(\omega)$ measures the medium's elastic response to shear forces, and $G''(\omega)$ measures its viscosity. They are natural probes of biofilms' responses to potential therapeutic agents. Similarly, the dynamic viscosity, $$\eta(\omega) = \frac{1}{\omega}\sqrt{G'^2(\omega) + G''^2(\omega)}, \quad (8)$$

provides an overall impression of a biofilm's ability to exchange material with its surroundings.

Figure 3A:
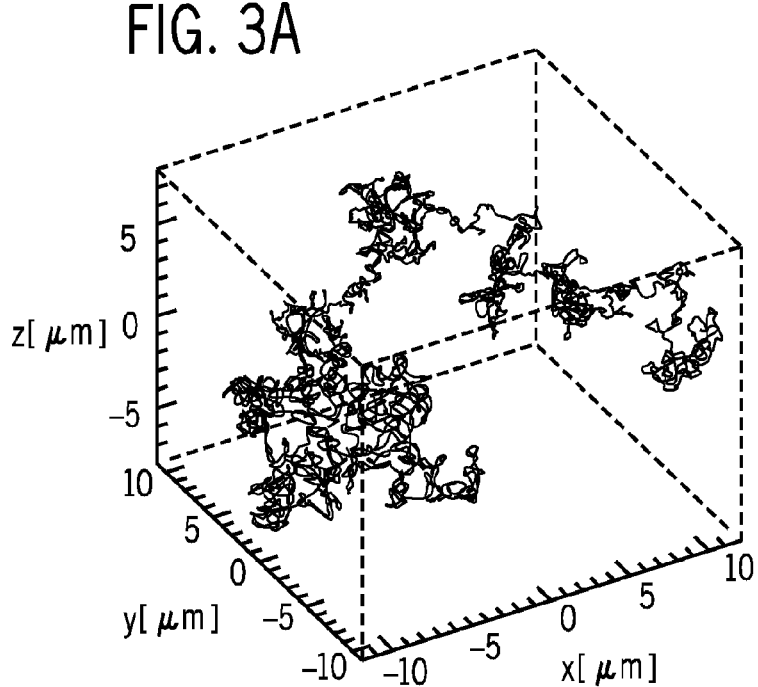
FIG. 3A illustrates a 3-D plot of a trajectory of a polystyrene bead freely diffusing in a Newtonian fluid.

To establish the accuracy of our holographic microrheology system, we first analyze the motions of a probe particle diffusing in a Newtonian fluid. The five-minute trajectory plotted in FIG. 3A was obtained for a single polystyrene sphere of nominal radius a=0.75 μm suspended in a density matched solution of 25% (w/w) glycerol in water whose viscosity is expected to be 1.7 mPa s. The particle was positioned with an optical tweezer at the midplane of a 50 μm thick sample volume to minimize hydrodynamic coupling to the glass walls and then was released to acquire data.

Figure 3B:
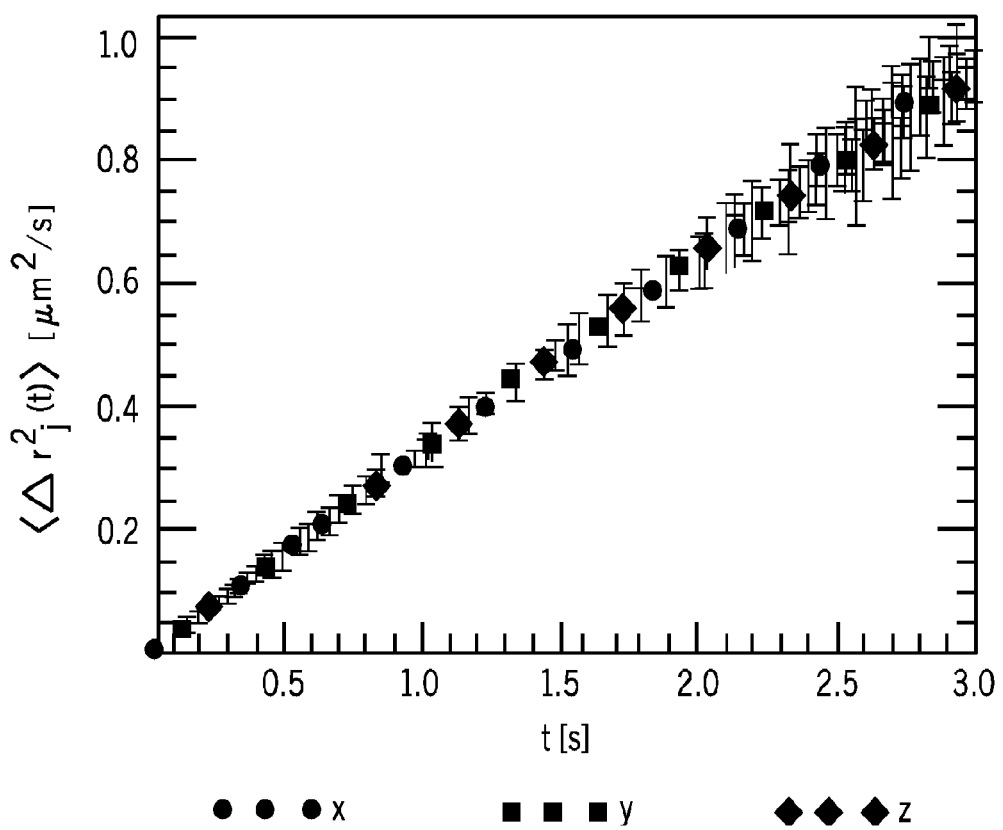
FIG. 3B shows mean-square displacement for each x, y, z coordinate as a function of time.

Fitting images to the Lorenz-Mie scattering formula yields an estimated single-image precision of $\in_x=\in_y=4$ nm and $\in_z=20$ nm. The mean-square displacement for each coordinate is plotted in FIG. 3B together with a fit to Eq. (3). All three traces are consistent with $D_0=0.1695\pm0.0001$ μm²/s. When combined with the trajectory average of the particle's measured radius, $a=0.775\pm0.014$ μm, this suggests an overall viscosity of $\eta=1.67\pm0.01$ mPa s. Given the shutter period of $t_s=1$ ms, the extrapolated offsets yield $\in_x=\in_y=8\pm4$ nm and $\in_z=35\pm8$ nm. These values are consistent with the estimated single-frame resolution and suggest that the accuracy of the position measurement is comparable to its precision.

The availability of high-resolution axial tracking data is one of the principal benefits of holographic particle tracking for microrheology. Consistency among the three data sets in this case confirms the measurements' freedom from hydrodynamic coupling to the surfaces. More generally such comparisons are useful for gauging a sample's isotropy and homogeneity.

Because results from the three coordinates are in agreement, we analyze the three-dimensional mean-squared displacement, $\langle\Delta r^2(t)\rangle = \Sigma_{j=1}^3 \langle\Delta r_j^2(t)\rangle$, with Eqs. (4), (6) and (8) to obtain the loss modulus, $G''(\omega)$, plotted in FIG. 4A and the dynamic viscosity, $\eta(\omega)$, plotted in FIG. 4B. As expected, the glycerol-water solution acts as a Newtonian fluid whose storage modulus, $G'(\omega)$, is too small to resolve over the range of frequencies probed. Its viscosity, $\eta(\omega)=1.680\pm0.001$ mPa s is therefore independent of frequency and agrees with values obtained from bulk measurements.

Figure 4C:
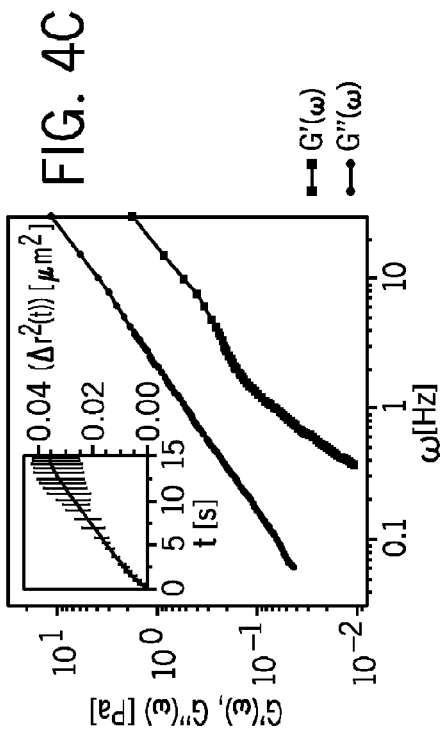
FIG. 4C shows viscoelastic moduli for a 17 wt. % sample of 250 k Da polyethylene oxide ("PEO") in water with the inset graph showing mean square displacement of the probe particle's trajectory.

Having established the accuracy of the three-dimensional particle tracking method and the mechanical stability of our instrument, its efficacy is shown particle-tracking microrheology by applying it to a standard non-Newtonian sample, an aqueous solution of high-molecular-weight PEO. FIG. 4C shows $G'(\omega)$ and $G''(\omega)$ obtained from a single sphere dispersed in a 17 wt % solution of 200 kDa PEO in deionized water. As for the Newtonian fluid, consistent results are obtained in all three coordinates, so that combined results are presented in FIGS. 4C and 4D.

The viscoelastic moduli, plotted in FIG. 4C, agree quantitatively with results reported for similar samples under comparable conditions. The loss modulus, $G''(\omega)$, exceeds the storage modulus, $G'(\omega)$, over the entire frequency range, which identifies this sample as a fluid, rather than a gel. The associated dynamic viscosity, plotted in FIG. 4D, decreases monotonically with increasing frequency, which is the signature of a shear-thinning fluid.

The data in FIG. 5 show comparable results for biofilm polysaccharides. Prior studies of biofilm's structure using other methods have revealed a degree of heterogeneity at the sub-millimeter scale that might seem unamenable to systematic physical analysis. Indeed, measurements of model biofilms' macroscopic rheological properties have yielded viscoelastic moduli differing by more than three orders of magnitude, even for nominally similar samples. These differences have been attributed to loading, strain rate, total strain and sample preparation.

Microrheology addresses many of these concerns by probing the local-scale properties of unloaded samples in equilibrium. Although particle-tracking microrheology has been applied to a wide range of industrially and biologically relevant materials, its application to biofilms appears to be novel. Model biofilms can be prepared without the complication of swimming bacteria, and so lend themselves to this kind of analysis.

An example study was performed on *Streptococcus mutans* polysaccharide samples which were extracted from 5-day-old biofilms of *S. mutans* UA159 (ATCC 700610) that were grown on glass slides in the presence of 10% sucrose. Water-soluble (S) polysaccharides were extracted with MilliQ water at room temperature. The insoluble (N) polysaccharide fraction then was extracted in 1N NaOH. Both extracts were neutralized to pH 7.0±0.5 and precipitated with cold ethanol (75% v/v) at −18° C. for at least 24 h. The resulting polysaccharide samples have a mean molecular weight of about 10 kDa with a polydispersity of at least 50 percent, and contain trace amounts of protein. After precipitation, the samples were washed several times with 75% (v/v) ethanol, blotdried and dissolved in water (S) or 1N NaOH (N), at 20% (w/v) to form the gels used in the microrheological measurements. Polystyrene probe particles were dispersed at random in the polysaccharide at this time, and particles near the mid-plane of the sealed sample chamber were selected for measurement.

Figure 4D:
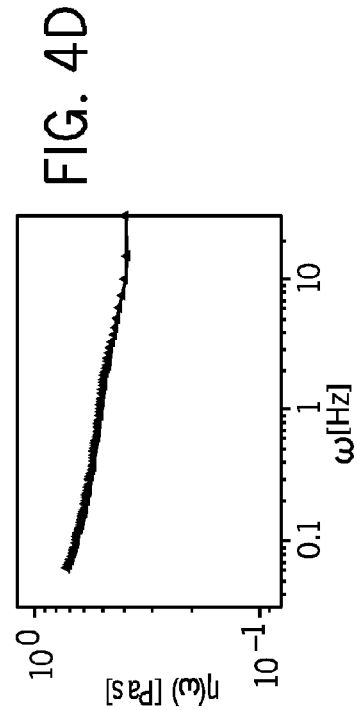
FIG. 4D shows the dynamic viscosity.
Figure 4A:
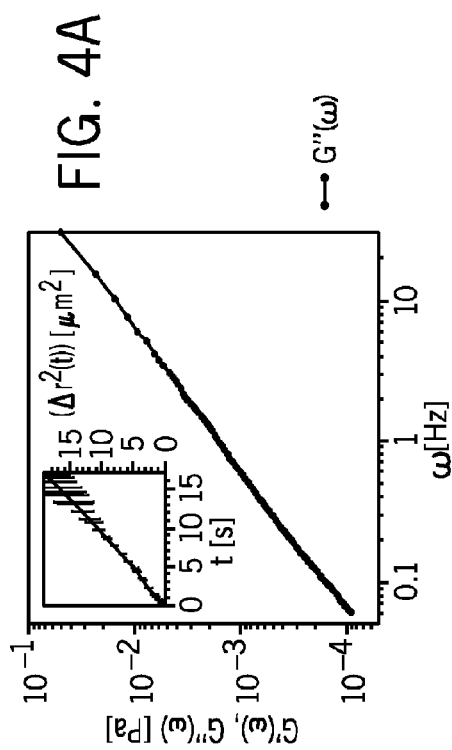
FIG. 4A shows a measure of the viscoelastic moduli, $G'(\omega)$ and $G''(\omega)$, extracted from the data of FIGS. 3A and 3B.
Figure 4B:
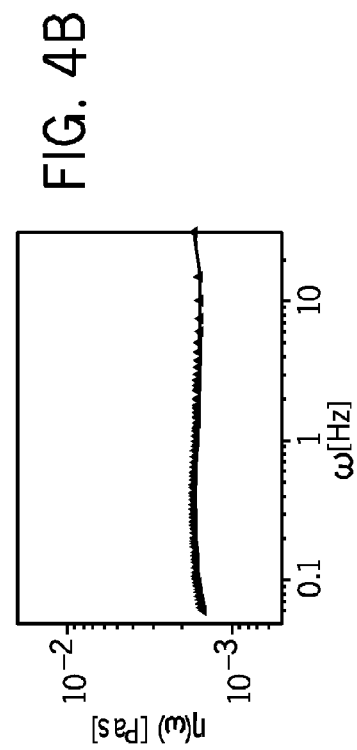
FIG. 4B shows associated dynamic viscosity, $\eta(\omega)$.
Figure 5C:
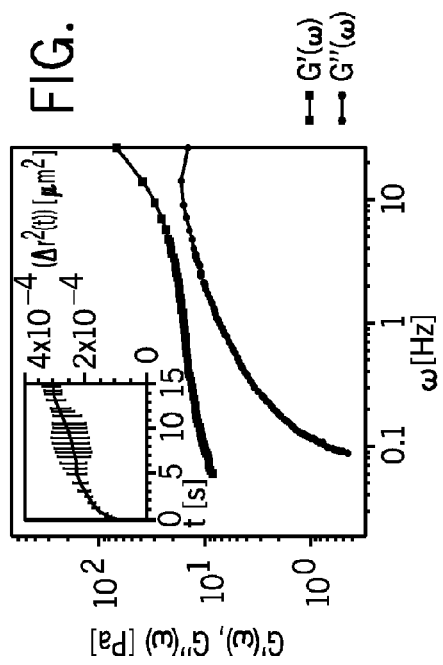
FIG. 5C shows the same variables as FIG. 5A for an N-type polysaccharide at same concentration and FIG. 5D shows the same variables as FIG. 5B for the same concentration for an N-type polysaccharide.
Figure 5D:
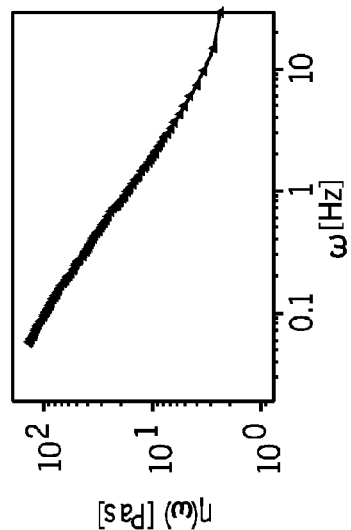
Figure 5A:
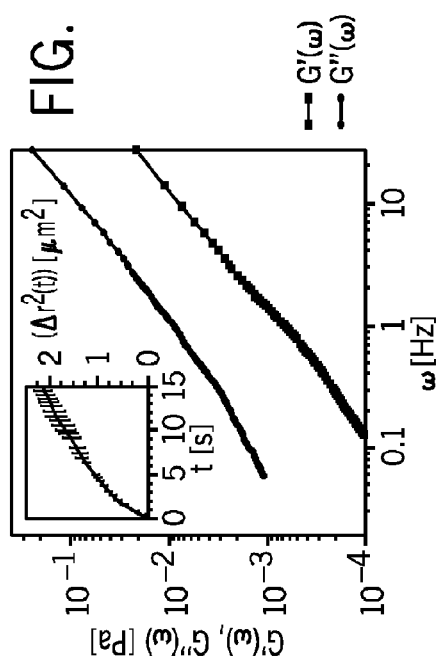
FIG. 5A shows viscoelastic moduli, $G'(\omega)$ and $G''(\omega)$, of a reconstituted S-type polysaccharide biofilm with a graph inset of the mean square displacement.
Figure 5B:
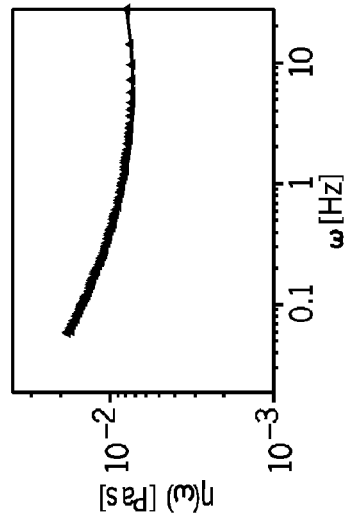
FIG. 5B shows dynamic viscosity of the S-type biofilm.

Results for the S fraction, plotted in FIGS. 5A and 5B, resemble those for the PEO solution in FIGS. 4C and 4D. The biofilm's water-soluble polysaccharides form a shear-thinning fluid roughly ten times more viscous than water.

The data in FIG. 5C, by contrast, show that the N-type fraction forms an elastic gel with a typical storage modulus of 10 Pa. This is several hundred times smaller than the mean value reported for bulk samples of *S. mutans* polysaccharides in other conventional prior art. It is consistent, however, with values reported at the lowest loadings when the substantial measurement error is taken into account. Accurate measurements at low loading are one of the strengths of microrheology, so that the results in FIGS. 5C and 5D are more likely to reflect the biofilm's properties in vivo. Even at low loading, the N-type gel is strongly shear-thinning, as indicated by its dynamic viscosity in FIG. 5D. This is a desirable trait for dental biofilms because it facilitates removal by brushing.

These observations suggest complementary roles of the two fractions in establishing the biofilm's mechanical and biological properties in vivo. The N-type material appears better suited to play the role of the mechanical scaffold within which the biofilm's bacterial colony establishes its ecosystem. Ability to disrupt the N-type gel, therefore, might be considered a promising characteristic for therapeutic agents. Microrheological assays of such agents' influence on N-type extracts should provide a simple and cost-effective screening technique. The ability of holographic microrheology to track multiple probe particles simultaneously furthermore creates opportunities for screening multiple therapeutic agents individually and in combination as a function of concentration.

B. Characterizing Milk Fat Globules

In another embodiment, we have used the method of the invention to analyze milk fat droplets from a range of commercial milk products including several grades of homogenized pasteurized cow's milk, sheep milk and goat milk. In each case, the sample was diluted by 1000:1 with deionized water before being sealed between a microscope slide and a glass cover slip and mounted on the stage of the microscope. Given the imaging system's calibrated magnification of 101 nm/pixel, a typical 640×480 pixel image, I(r), captures roughly 10 resolvable globules.

Unprocessed holograms suffer from large intensity variations due to speckle, interference effects in the microscope's optics and scattering by dust and other imperfections. We correct for these by normalizing I(r) with a background hologram $I_0(r)$ obtained with no sample in the field of view. As described in part hereinbefore, the normalized hologram then can be fit to the prediction of Lorenz-Mie theory, $$\frac{I(r)}{I_0(r)} = 1 + 2\alpha \mathcal{R}\{f_s(r - r_p) \cdot \hat{\varepsilon} e^{-ikz_p}\} + \alpha^2 |f_s(r - r_p)|^2, \quad (9)$$

where $k = 2\pi n_m/\lambda$ is the wavenumber of light in a medium of complex refractive index $n_m$, and where $f_s(r - r_p)$ is the Lorenz-Mie scattering function describing how light of polarization $\hat{\varepsilon}$ is scattered by a sphere located at $r_p$. In practice, the illuminating beam is not perfectly uniform, and the factor $\alpha \approx 1$ can be used to account for variations in $I_0(r_p)$, such as position-dependent variations. Assuming the scatterer to be a uniform and homogeneous dielectric sphere illuminated by light that is linearly polarized in the $\hat{x}$ direction, $$f_s(r) = \sum_{n=1}^{\infty} f_n (i a_n N_{e1n}^{(3)}(r) - b_n M_{o1n}^{(3)}(r)), \quad (10)$$

where $f_n = i^n (2n+1)/[n(n+1)]$, and where $M_{o1n}^{(3)}(r)$ and $N_{e1n}^{(3)}(r)$ are well known vector spherical harmonics, $$M_{o1n}^{(3)}(r) = \frac{\cos\phi}{\sin\theta} P_n^1(\cos\theta) j_n(kr)\hat{\theta} - \sin\phi \frac{dP_n^1(\cos\theta)}{d\theta} j_n(kr)\hat{\phi} \quad (11)$$

$$N_{e1n}^{(3)}(r) = n(n+1)\cos\phi P_n^1(\cos\theta) \frac{j_n(kr)}{kr} \hat{r} + \cos\phi \frac{dP_n^1(\cos\theta)}{d\theta} \frac{1}{kr} \frac{d}{dr}[rj_n(kr)]\hat{\theta} - \frac{\sin\phi}{\sin\theta} P_n^1(\cos\theta) \frac{1}{kr} \frac{d}{dr}[rj_n(kr)]\hat{\phi}. \quad (12)$$

Here, $P_n^1(\cos\theta)$ is the associated Legendre polynomial of the first kind, and $j_n(kr)$ is the spherical Bessel function of the first kind of order n. The expansion coefficients in Equation (10) are given by conventional well known relationship, $$a_n = \frac{m^2 j_n(mka)[kaj_n(ka)]' - j_n(ka)[mkaj_n(mka)]'}{m^2 j_n(mka)[kah_n^{(1)}(ka)]' - h_n^{(1)}(ka)[mkaj_n(mka)]'} \quad (13)$$

and by $$b_n = \frac{j_n(mka)[kaj_n(ka)]' - j_n(ka)[mkaj_n(mka)]'}{j_n(mka)[kah_n^{(1)}(ka)]' - h_n^{(1)}(ka)[mkaj_n(mka)]'} \quad (14)$$

where $m = n_p/n_m$ is the particle's refractive index relative to the medium, $j_n(x)$ is the spherical Bessel function of the first type of order n, $h_n^{(1)}(x)$ is the spherical Hankel function of the first type of order n, and where primes denote derivatives with respect to the argument. The sum in Eq. (2) converges after a number of terms, $n_c = ka + 4.05(ka)^{1/3} + 2$, which depends on the particle's size. The only challenge in this computation is to calculate the Bessel functions and their ratios both accurately and efficiently. Most preferably one uses an accurate, computationally intensive continued fraction algorithm which is a conventional method from Lentz to compute the $a_n$ and $b_n$ coefficients. In addition, the more efficient recursive algorithm due to Wiscombe can be used for the spherical Bessel functions. This trade-off ensures that we can obtain accurate results using our apparatus for spheres ranging in diameter from 10 nm to more than 10 μm and refractive indexes exceeding $n_p = 2.6$.

To characterize a sphere, we fit its normalized hologram to Eqs. (9) through (14) for $r_p$, $n_p$, a, and α, using a standard Levenberg-Marquardt least-squares algorithm. Despite the fairly large number of free parameters, these fits converge rapidly and robustly, and typically yield the particle's position and size with nanometer-scale resolution, and its refractive index to within one part in a thousand.

Figure 6B:
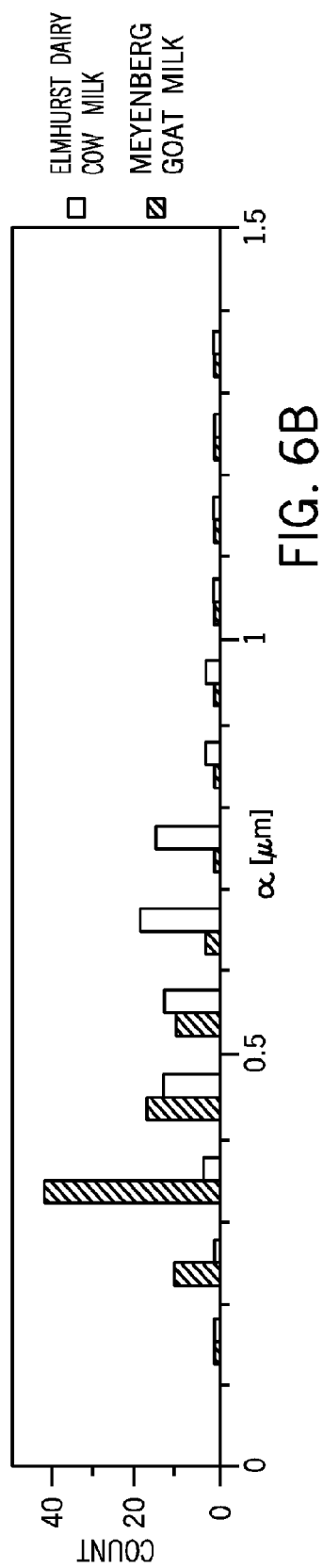
FIG. 6B shows count distribution versus diameter and FIG. 6C shows count distribution versus refractive index.
Figure 6C:
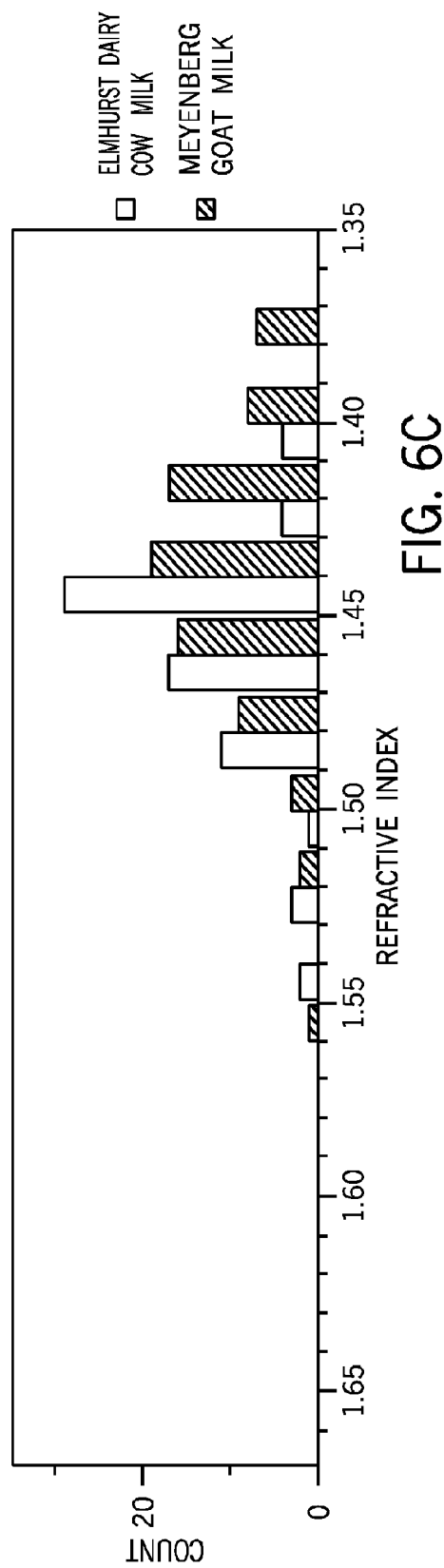

We applied this technique to 5 samples of commercially processed milk obtained from a local supermarket. These include pasteurized homogenized cow's milk with designated fat contents ranging from fat-free to whole milk, as well as goat's milk. Up to 100 randomly selected fat droplets were analyzed for each sample to obtain estimates for the size and refractive index distributions for the fat droplets in each sample. The results are summarized in FIGS. 6A-6C and Table I.

TABLE I

Globule radius and refractive index for commercial milk samples.

| Sample | Radius [μm] | Refractive Index |
|---|---|---|
| Elmherst Whole | 0.693 ± 0.174 | 1.468 ± 0.035 |
| Elmherst 2% | 0.643 ± 0.183 | 1.460 ± 0.029 |
| Elmherst 1% | 0.590 ± 0.131 | 1.465 ± 0.034 |
| Elmherst Fat Free | 0.562 ± 0.140 | 1.460 ± 0.031 |
| Meyenberg Goat Fresh | 0.576 ± 0.137 | 1.425 ± 0.038 |
| Meyenberg Goat 1 Mo. | 0.441 ± 0.088 | 1.451 ± 0.036 |
| Type B Immersion Oil | | 1.521 ± 0.017 |

The radius of the fat globules increases with increasing fat content, as does the dispersion of the radius. The mean refractive index of the individual globules from cow's milk, n=1.464 agrees with sample-averaged values for single-droplet refractive indexes obtained by light scattering. It substantially exceeds the range of 1.3444 to 1.3525 obtained for the overall refractive index of bulk samples. Such values are dominated by the optical properties of water, whose refractive index at room temperature is $n_m = 1.333$. Holographic measurements, by contrast, yield values for individual droplets, and so offer a more detailed view of the fat's properties than either of these previously reported methods. Indeed, it is possible to distinguish goat's milk from cow's milk on this basis, the goat's milk having a resolvably lower mean refractive index.

Interestingly, this relationship changes as the milk ages. Table I shows that the mean refractive index of goat milk droplets increases over the course of a month, rising to 1.45. This result demonstrates that holographic characterization can be useful not only for distinguishing types of milk, but also can be used to assess a sample's age (which is associated with chemical changes).

Having access to particle-resolved data also reveals an interesting correlation between the size of the fat globules and the dispersion of their estimated refractive indexes. Larger particles' apparent refractive indexes are consistent with each other to within the resolution of the measurement technique. Smaller droplets display a substantially larger range of refractive indexes.

Figure 7A:
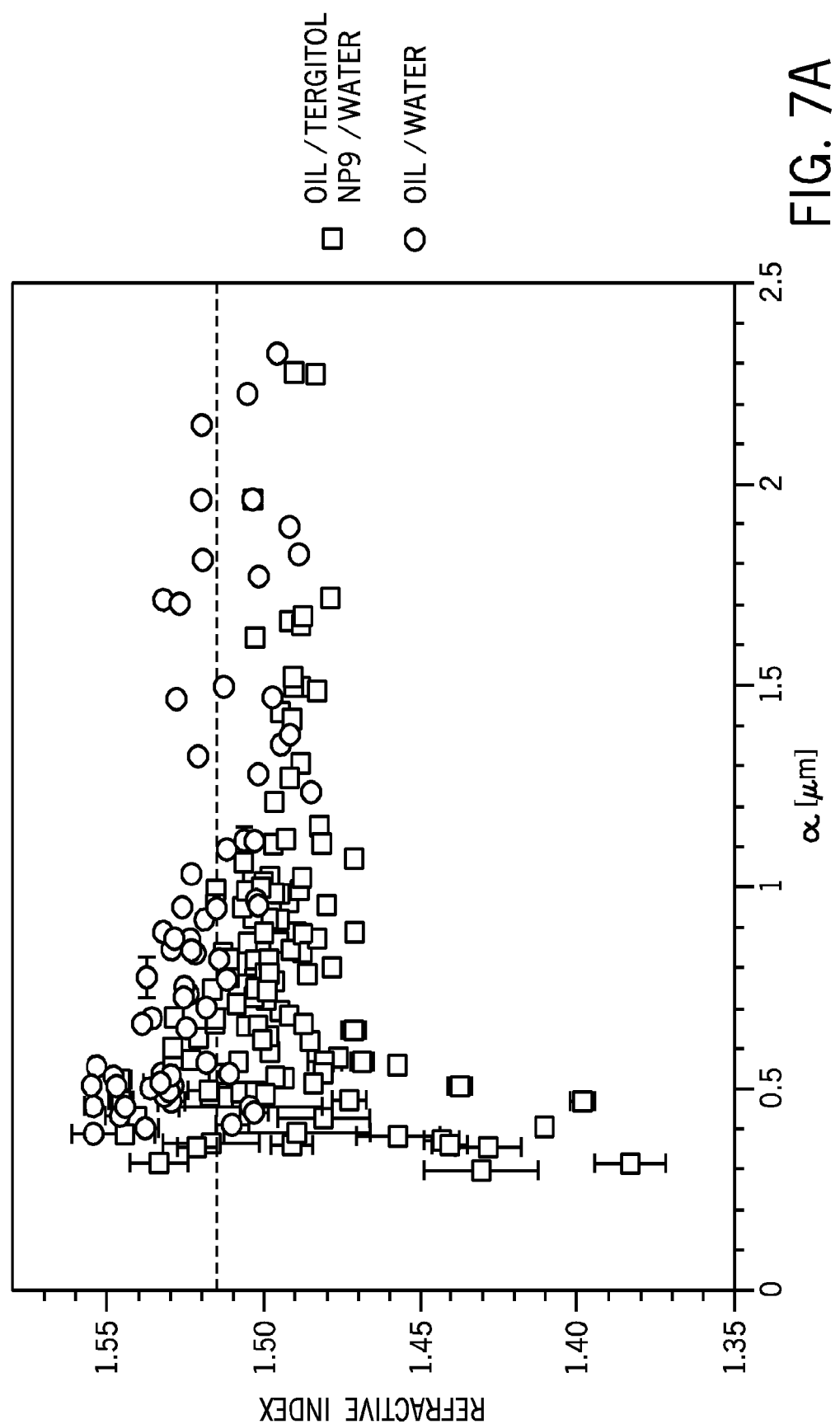
FIG. 7A shows refractive index versus droplet radius for dispersed type B immersion oil in water, with and without a surfactant.

This is not an inherent limitation of the measurement technique, as the data in FIGS. 7A-7C demonstrate. The circular data points were obtained for droplets of Cargille Type B microscope immersion oil that were dispersed as spherical droplets in water by vigorous shearing. This oil has a nominal bulk refractive index of 1.515 for red light at a temperature of 25±C. This value is consistent with the single-droplet results obtained over the entire range of droplet radii considered in this study, ranging from 0.25 μm to 2.5 μm. Variations from droplet to droplet may be ascribed to imperfect correction of intensity variations in the illumination by Eq. (9).

Results more reminiscent of those for milk fat droplets are obtained when the oil droplets are stabilized with surfactant. The square points in FIG. 7A were obtained for Type B oil with the addition of 0.1% (v/v) Tergitol NP9, a nonionic surfactant whose bulk refractive index is 1.491. The addition of this surfactant reduces the single-droplet refractive index for larger particles. It also increases the range of refractive indexes measured for smaller particles.

This observation leads us to conclude that holographic particle characterization is sensitive to surface properties, and, in particular, to surface coverage by surfactants. In the case of milk droplets, this suggests that holographic microscopy is sensitive to the milk fat globule membrane (MFGM). This sensitivity is noteworthy because, at just 10 to 20 nm thickness, the MFGM is much thinner than the wavelength of light and constitutes a very small proportion of the droplets' volume.

The variability in results obtained for smaller droplets most likely reflects the breakdown of assumptions underlying the derivation of Eqs. 10 through 14. This form of the Lorenz-Mie scattering theory is appropriate for a homogeneous isotropic sphere with an abrupt interface. Using this result to interpret holograms of coated spheres consequently can lead to inconsistencies in the extracted parameters. This effect should be more pronounced for smaller spheres whose surface-area-to-volume ratio is higher. Applying a more sophisticated form of the scattering function that accounts for core-shell structure should reduce this variability at the expense of considerable additional computational complexity.

Smaller milk fat droplets also display systematically larger refractive indexes than larger droplets. This may reflect size-dependent variation in the fatty acid composition of the MFGM and triglyceride core. Even the simplest implementation of holographic characterization therefore can be useful for assessing milk fat droplet composition.

Still more information could be obtained by performing holographic characterization of individual droplets at multiple wavelengths simultaneously. The resulting spectroscopic information could be useful for further quantifying the composition of individual globules. Even in its simplest form, however, fat globule characterization through holographic microscopy provides a particle-by-particle analysis of milk fat composition that is not otherwise available. It requires little specialized equipment, and so can be easily adapted for process control and quality assurance applications.

The particular application of holographic characterization to milk demonstrates that it is possible to determine both the type (cow, goat, etc.) and quality (fat-free, whole, fresh, old, etc.) of milk samples based on holographic analysis. This observation suggests particular applications of holographic characterization to quality assurance and process control in dairy industries. More generally, the broader use of holographic characterization for other emulsion-based systems, such as paint, other foods, and cosmetics is clearly applicable based on this disclosure herein.

It should also be noted that holographic characterization is sensitive to the surface properties of emulsion droplets, as well as to their bulk properties. Surface characterization can include identifying the existence of a surface coating, measurement of surface coverage, and characterization of the nature of surface coating. Fitting to a more sophisticated form of the theory can provide quantitative information on the thickness and composition of surface coatings. This is useful for milk characterization, and it also should be useful in other contexts (indicated above) where the surface of a particle can differ from its bulk.

C. Characterizing Colloidal Particles

In yet another embodiment, a polystyrene sulfate sphere dispersed in water was analyzed and characterized. As described hereinbefore, digitized holograms yield a particle's three-dimensional position, $r_p$, its radius, a, and its index of refraction, $n_p$. We assume that the incident field, $E_0(r) = u_0(p) \exp(ikz)\hat{\epsilon}$, is uniformly polarized in the $\hat{\epsilon}$ direction and varies slowly enough over the size of the particle to be treated as a plane wave propagating along the $\hat{z}$ direction. Its amplitude $u_0(\rho)$ at position $\rho = (x, y)$ in the plane $z = z_p$ of the particle is thus the same as its amplitude in the focal plane, $z = 0$. The wave propagates along the $\hat{z}$ direction with wave number $k = 2\pi n_m/\lambda$, where $\lambda$ is the light's wavelength in vacuum and $n_m$ is the refractive index of the medium. For pure water at 25° C., $n_m = 1.3326$ at $\lambda = 0.632$ μm.

The particle at $r_p$ scatters a portion of the incident field into a highly structured outgoing wave, $E_s(r) = \alpha \exp(-ikz_p) u_0(r_p) f_s(r - r_p)$, where $\alpha = 1$ accounts for variations in the illumination, and where $f_s(r)$ is the Lorenz-Mie scattering function, which depends on a, $n_p$, $n_m$ and $\lambda$. The scattered field generally covers a large enough area at the focal plane that the interference pattern, $$I(\rho) = |E_s(r) + E_0(r)|^2|_{z=0}, \tag{15}$$

is dominated by long-wavelength variations in $|u_0(\rho)|^2$. The resulting distortions have been characterized, but were not corrected in previous analyses of $I(\rho)$. Fortunately, $|u_0(\rho)|^2$ can be measured in an empty field of view, and the in-line hologram can be normalized to obtain the undistorted image, $$B(\rho) \equiv \frac{I(\rho)}{|u_0(\rho)|^2} \tag{16}$$

$$= 1 + \frac{2\mathcal{R}\{E_s(r) \cdot E_0^*(r)\}}{|u_0(\rho)|^2} + \frac{|E_s(r)|^2}{|u_0(\rho)|^2}, \tag{17}$$

on the plane $z = 0$. If we further assume that the phase of the collimated incident beam varies slowly over the field of view, the normalized image is related to the calculated Mie scattering pattern, $f_s(r)$, in the plane z=0 by, $$B(\rho) \approx 1 + 2\alpha \} \{f_s(r-r_p) \cdot \hat{\epsilon} e^{-ikz_p} + \alpha^2 |f_s(r-r_p)|^2 \quad (18)$$

Eq. (18) can be fit to measured holograms by treating the particle's three-dimensional position, its radius and its refractive index as free parameters. Previous studies fit non-normalized holograms to phenomenological models or Mie scattering theory for some of these quantities, but never all five. Because errors in the adjustable parameters are strongly correlated, failing to optimize them all simultaneously yields inaccurate results. Fitting instead to the full Lorenz-Mie theory provides more information with greater precision.

Numerical fits to digitized and normalized holographic images were performed with the Levenberg-Marquardt nonlinear least-squares minimization algorithm using the camera's measured signal-to-noise ratio to estimate single-pixel errors. The $\chi^2$ deviates for all of the fits we report are of order unity, so that the calculated uncertainties in the fit parameters accurately reflect their precision.

Because the laser's wavelength and the medium's refractive index are both known, the only instrumental calibration is the overall magnification. This contrasts with other three-dimensional particle tracking techniques, which require independent calibrations for each type of particle, particularly to track particles in depth.

The image in FIG. 8A(1) (and accompanying data of 8A(2) and 8A(3)) shows the normalized hologram, $B(\rho)$, for a polystyrene sulfate sphere dispersed in water at height $z_p=22.7$ μm above the focal plane. This sphere was obtained from a commercial sample with a nominal diameter of $2a=1.48\pm0.03$ μm (Bangs Labs, Lot PS04N/6064). The camera's electronic shutter was set for an exposure time of 0.25 msec to minimize blurring due to Brownian motion. After normalizing the raw 8-bit digitized images, each pixel contains roughly 5 significant bits of information. The numerical fit to $B(\rho)$ faithfully reproduces not just the position of the interference fringes, but also their magnitudes. The quality of the fit may be judged from the azimuthal average; the solid curve is an angular average about the center of $B(\rho)$, the dashed curves indicate the standard deviations of the average, and the discrete points are obtained from the fit.

The fit value for the radius, $a=0.73\pm0.01$ μm, (see FIG. 8A(2)) falls in the sample's specified range, which reflected a lower bound of $0.69\pm0.07$ μm obtained with a Beckman Z2 Coulter Counter and an upper bound of $0.76\pm0.08$ μm obtained by analytical centrifugation. Agreement between the quoted and measured particle size suggests that the present measurement's accuracy is comparable to its precision. In that case, both precision and accuracy surpass results previously obtained through analysis of $I(\rho)$. The trajectory-averaged value for the refractive index, $n_p=1.55\pm0.03$, also is consistent with the properties of polystyrene colloid inferred from light scattering measurements on bulk dispersions.

Comparable precision in measuring a single particle's refractive index has been achieved by analyzing a colloidal particle's dynamics in an optical trap. This method only can be applied to particles with comparatively small refractive indexes, however, because particles with relative refractive indexes greater than $n_p \approx 1.3 n_m$ are difficult to trap. Holographic characterization, by contrast, requires only a single holographic snapshot rather than an extensive time series, does not require optical trapping, and so does not require separate calibration of the trap, and is effective over a wider range of particle sizes and refractive indexes.

Additional data in FIGS. 8B(1) through 8B(3) were obtained for a 1.45 μm diameter $TiO_2$ sphere at $z_p=7$ μm above the focal plane. This sample was synthesized from titanium tetraethoxide and was heat-treated to increase its density. Strong forward scattering by such high-index particles gives rise to imaging artifacts unless the medium is index matched to the cover slip. Dispersing the particle in immersion oil ($n_m=1.515$) eliminates these artifacts, but introduces spherical aberration for the lens we used, which must be corrected to obtain reliable results. The fit diameter of $1.45\pm0.03$ $n_m$ and refractive index of $2.01\pm0.05$ are consistent with results obtained by electron microscopy and bulk light scattering, respectively. This result is noteworthy because no other single-particle characterization method works for such high refractive indexes.

The data in FIGS. 8C(1) through 8C(3) show results for a nominally 5 μm silica sphere (Bangs Labs, Lot SS05N/4364) dispersed in water at $z_p=38.8$ μm above the focal plane. The fit refractive index, $n_p=1.434\pm0.001$, is appropriate for porous silica and the diameter, $a=4.15\pm0.01$ μm agrees with the $4.82\pm0.59$ μm value obtained for this sample with a Beckman Z2 Coulter Counter. We have successfully applied holographic characterization to colloidal spheres as small as 100 nm in diameter and as large as 10 μm. Unlike model-based analytical methods, fitting to the exact Lorenz-Mie scattering theory is robust and reliable over a far wider range of particle sizes, provided that care is taken to maintain numerical stability in calculating $f_s(r)$.

The same fits resolve the particle's position with a precision of 1 nm in-plane and 10 nm along the optical axis. Comparable nanometer-scale tracking resolution can be obtained with conventional illumination, but requires detailed calibrations for each particle. Another benefit of holographic imaging is its very large depth of focus compared with conventional microscopy. Our system provides useful data over a range of more than 100 μm, which contrasts with the ±3 μm useful depth of focus using conventional illumination.

Holographic video microscopy lends itself to three-dimensional particle tracking, as the data in FIGS. 9A(1) through 9B(2) demonstrate for a colloidal silica sphere (Bangs Labs, Lot SS04N/5252) dispersed in water. This particle was lifted 30 μm above the focal plane with an optical tweezer, and then released and allowed to sediment. The images in FIGS. 9A(1) and 9B(1) show the particle near the beginning of its trajectory and near the end. Fits to Eq. 18 are shown in FIGS. 9A(2) and 9B(2).

Figure 11:
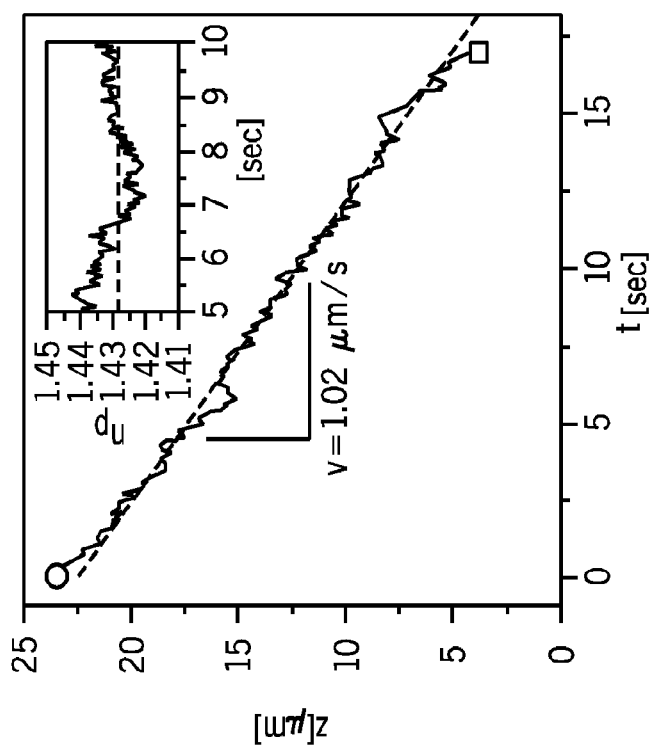
FIG. 11 shows the function z(t) thermal fluctuation associated with thermal sedimentation (inset graph is a fit of the refractive index which is independent of position)

The particle's measured trajectory in 1/30 s intervals during 15 s of its descent is plotted in FIG. 10. Its vertical position $z(t)$, FIG. 11, displays fluctuations about a uniform sedimentation speed, $v=1.021\pm0.005$ μm/s. This provides an estimate for the particle's density through $\rho_p=\rho_m+9$ nv/$(2a^2 g)$ where $\rho_m=0.997$ g/cm$^3$ is the density of water and $\eta=0.0105$ P is its viscosity at T=21° C., and where g=9.8 m/s$^2$ is the acceleration due to gravity. The fit value for the particle's radius, at $a=0.729\pm0.012$ μm, remained constant as the particle settled. This value is consistent with the manufacturer's specified radius of $0.76\pm0.04$ μm, measured with a Beckman Z2 Coulter Counter. Accordingly, we obtain $\rho_p=1.92\pm0.02$ g/cm$^3$, which is a few percent smaller than the manufacturer's rating for the sample. However, the fit value for the refractive index, $n_p=1.430\pm0.007$, also is 1.5% below the rated value, suggesting that the particle is indeed less dense than specified.

Figure 12:
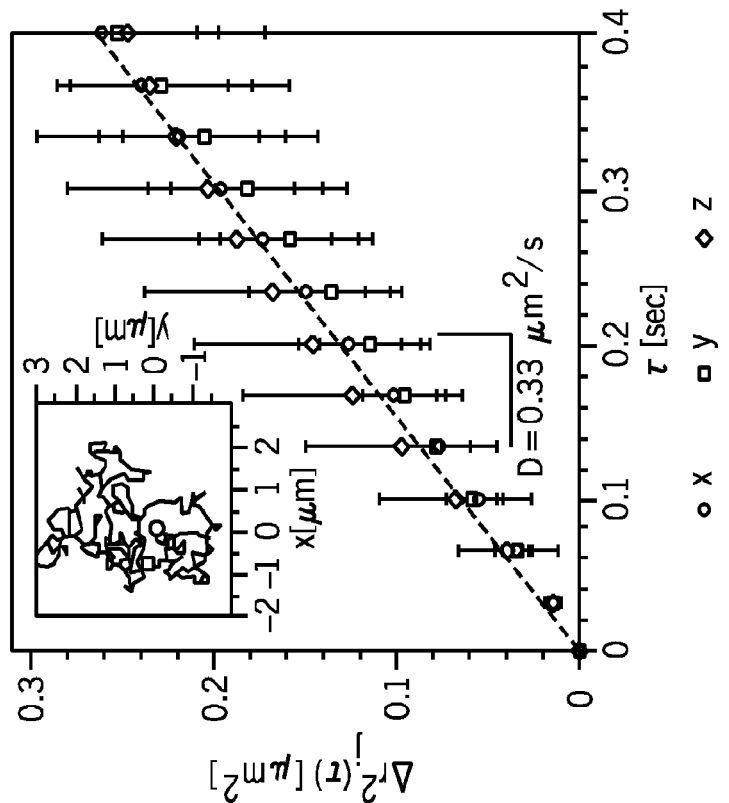
FIG. 12 shows mean square positional fluctuations as a function of $\tau$ (sec.) with Einstein-Smoluchowsky x, y, z scaling and with an inset plot of the x, y plane of trajectory projections.

The mean-square displacements, $\Delta r_j^2(\tau) = \langle (r_j(t+\tau) - r_j(t))^2 \rangle$, of the components of the particle's position provide additional consistency checks. As the data in FIG. 12 shows, fluctuations in the trajectory's individual Cartesian components agree with each other, and all three display linear Einstein-Smoluchowsky scaling, $\Delta r_j^2(r)=2D\tau$, a diffusion coefficient $D=0.33\pm0.03$ µm²/s. This is consistent with the anticipated Stokes-Einstein value, $D_0=k_B T/(6\pi\eta\alpha)=0.30\pm0.03$ µm²/s, where $k_B$ is Boltzmann's constant. The offsets obtained from linear fits to $\Delta r_j^2(t)$ also are consistent with no worse than 1 nm accuracy for in-plane positions and 10 nm for axial positions throughout the trajectory. The optical characterization of the particle's properties thus is consistent with the particle's measured dynamics.

Precise measurements of probe particles' three-dimensional trajectories made possible by video holographic microscopy lend themselves naturally to applications in particle-imaging microrheology. Applying this technique to biofilms, in particular, shows promise for high-throughput combinatorial screening of candidate therapeutic or remedial agents. Rather than assessing their biological or biochemical influence, holographic microrheology offers direct insight into these agents' influence on biofilms' physical properties. In the case of dental biofilms, the availability of model polysaccharide gels will greatly simplify the development of standard assays for therapeutic agents. Because microrheological measurements require only micrometer-scale samples, very large arrays of independent assays should be possible in centimeter-scale systems, with each assay requiring just a few minutes of holographic recording.

The techniques we have described are readily extended for particles and media whose refractive indexes have large imaginary components. Extensions for core-shell particles and particles with more complex shapes, such as cylindrical nanowires, similarly should be feasible.

We have demonstrated that a single snapshot from an in-line holographic microscope can be used to measure a colloidal sphere's position and size with nanometer-scale resolution, and its refractive index with precision typically surpassing 1 percent.

A video stream of such images therefore constitutes a powerful six-dimensional microscopy for soft-matter and biological systems. Holographic particle tracking is ideal for three-dimensional microrheology, for measuring colloidal interactions and as force probes for biophysics. The methods we have described can be applied to tracking large numbers of particles in the field of view simultaneously for highly parallel measurements. Real-time single-particle characterization and tracking of large particle ensembles will be invaluable in such applications as holographic assembly of photonic devices. Applied to more highly structured samples such as biological cells and colloidal heterostructures, they could be used as a basis for cytometric analysis or combinatorial synthesis.

In addition, the concept of multi-wavelength holographic characterization can be applied to obtain spectroscopic information, such as the dependence of refractive index on wavelength. This can be useful for quantifying nutrient concentration in milk and related systems. It can be useful for distinguishing adulterants from pure products. Multiwavelength characterization also provides an opportunity for calibration-free measurements. The concept is that the particle's measured size should be independent of laser wavelength. If the wavelengths of the lasers used to illuminate the sample are known, then the overall length-scale calibration can be obtained form the condition that the particle's apparent radius should be the same at all wavelengths.

While preferred embodiments have been illustrated and described, it should be understood that changes and modifications can be made therein in accordance with one of ordinary skill in the art without departing from the invention in its broader aspects. Various features of the invention are defined in the following claims.

What is claimed:

1. A method for characterizing a specimen, comprising:
providing a holographic microscope;
providing a collimated laser beam to the holographic microscope;
scattering the collimated laser beam off the specimen to generate a scattered portion;
generating an on-axis hologram including an interference pattern from an unscattered portion of the collimated laser beam and the scattered portion;
recording the interference pattern for subsequent analysis wherein the step of recording the interference pattern includes a step of normalizing the interference pattern by dividing the interference pattern by a background form of interference pattern wherein the background form is selected from the group of a previously recorded background image form, a normalization constant form and a numerical model for a background illumination pattern form, and the normalized interference pattern is selectively fitted to a particular prediction methodology of light scattering, thereby providing characteristic information about the specimen; and
using the characteristic information for measuring at least one of a spatial location, a mechanical property, an optical property and a chemical property of the specimen.

2. The method as defined in claim 1 wherein the step of recording the interference pattern further includes obtaining information on at least one of size of the specimen and on complex refractive index of the specimen.

3. The method as defined in claim 1 further including the step of applying a scattering function to analyze the recorded interference pattern.

4. The method as defined in claim 3 wherein the scattering function comprises a Lorenz-Mie function.

5. The method as defined in claim 1 wherein the holographic microscope includes a focal plane and the step of measuring comprises identifying axial displacement of the specimen relative to the focal plane wherein the specimen comprises a particle disposed within a medium.

6. The method as defined in claim 5 wherein the step of identifying axial displacement does not require at least one of calibration or limitation of depth of focus of the holographic microscope.

7. The method as defined in claim 1 wherein the step of measuring comprises at least one of (1) identifying in one single time snapshot a position of a particle in the specimen and characterizing properties of the particle, thereby generating particle data; and (2) identifying in a plurality of time snapshots a trajectory of a particle in the specimen and characterizing properties along the trajectory, thereby generating particle data; and (3) wherein the specimen comprises a medium holding a colloidal suspension of particles and the step of measuring comprises analyzing at least one of the medium and interaction between the particles of the suspension.

8. The method as defined in claim 1 further including the steps of at least one of analyzing interaction between a particle of the specimen and a surface, interaction between at least two of the particles, velocity field of a fluid of the specimen and viscoelastic properties of a medium of this specimen.

9. The method as defined in claim 1 wherein the step of measuring includes at least one of simultaneously measuring the size of the specimen and the spatial location of the specimen, performing multi-point assays of rheological properties, performing an in situ measurement of a property of the specimen, analyzing a property of the specimen, analyzing a property of a probe particle, analyzing a property of the probe particle by evaluating thermally driven fluctuations of a property of the specimen, thereby determining visoelastic properties of a medium comprising the specimen; determining mean square fluctuation $\Delta r^2(t)$, thereby enabling characterization of a medium containing the probe particle; measuring streamlines in flowing fluids of the specimen, assessing the thermodynamic stability of colloidal dispersions of the specimen against aggregation and flocculation, measuring interactions among colloidal particles of the specimen, measuring colloidal particles' interactions with surfaces of the specimen, assessing particles responses to external fields and forces of the specimen, characterizing the particles' viscous drag characteristics of the specimen, and using particles' motions as probes of the viscoelastic and rheological properties of a medium comprising the specimen.

10. The method as defined in claim 1 wherein the step of measuring the optical property comprises determining at least one of refractive index and radius of a particle comprising the specimen and measured as a function of at least one of temperature, chemical composition and chemical concentration, thereby enabling characterization of at least one of stability of the specimen, chemical changes of the specimen and different chemical states for a family of selectable materials of the specimen.

11. The method as defined in claim 1 wherein the collimated laser beam includes using a plurality of different light wavelengths to obtain spectroscopic information about the specimen.

12. The method as defined in claim 1 wherein the scope of measuring the spatial location comprises dynamic tracking of a particle in a medium, thereby enabling characterization of properties of the particle.

13. The method as defined in claim 1 wherein the step of measuring includes analyzing at least one of the particle hydrodynamic radius, radius and refractive index.

14. A method for optically characterizing a specimen disposed in a medium, including the steps of providing a holographic microscope, providing a laser beam to the holographic microscope, scattering a collimated laser beam off the specimen in the medium to generate a scattered portion; generating an on-axis hologram including an interference pattern from an unscattered portion of the collimated laser beam and the scattered portion; recording the interference pattern for subsequent analysis wherein the step of recording the interference pattern includes a step of normalizing the interference pattern by dividing the interference pattern by a background form of interference pattern wherein the background form is selected from the group of a previously recorded background image form, a normalization constant form and a numerical model for a background illumination pattern form, and the normalized interference pattern is selectively fitted to a particular prediction methodology of light scattering, thereby providing characteristic information about the specimen; and using the characteristic information for measuring at least one of a spatial location of the specimen, a mechanical property of the specimen, an optical property of the specimen, a chemical property of the specimen, and a characteristic interaction between the specimen and the medium and a feature of the medium.

15. The method as defined in claim 14 further including the step of applying a Lorenz-Mie scattering function to analyze the recorded interference pattern.

16. The method as defined in claim 14 further including the step of at least one of analyzing interaction between a particle of the specimen and a surface, interaction between at least two of the particles, velocity field of a fluid of the specimen and viscoelastic properties of a medium of the specimen.

17. The method as defined in claim 14 wherein the specimen comprises a medium holding a colloidal suspension of particles and the step of measuring comprises analyzing at least one of the medium and interaction between the particles of the suspension.

18. The method as defined in claim 14 wherein the step of measuring includes at least one of measuring streamlines in flowing fluids of the specimen, assessing the thermodynamic stability of colloidal dispersions of the specimen against aggregation and flocculation, measuring interactions among colloidal particles of the specimen, measuring colloidal particles' interactions with surfaces of the specimen, assessing particles responses to external fields and forces of the specimen, characterizing the particles' viscous drag characteristics of the specimen, using particles' motions as probes of the viscoelastic and rheological properties of a medium determining at least one of refractive index and radius of a particle comprising the specimen and measured as a function of at least one of temperature, chemical composition and chemical concentration, thereby enabling characterization of at least one of stability of the specimen, chemical changes of the specimen and different chemical states for a family of selectable materials of the specimen.

19. The method as defined in claim 14 wherein the step of measuring comprises at least one of simultaneously measuring the size of the specimen and the spatial location of the specimen, performing multi-point assays of rheological properties, the specimen comprising a plurality of particles and the step of measuring comprises performing a measurement on each of the particles individually; and analyzing a property of a probe particle including evaluating thermally driven fluctuations of a property of the specimen, thereby determining viscoelastic properties of a medium comprising the specimen.

20. A computer readable medium comprised of a non-transitory storage medium for processing information to characterize a specimen comprising, a computer software module including computer software having a set of instructions for operating on non-transitory data characteristic of the specimen;

the non-transitory data characteristic of the specimen related to an on-axis hologram including an interference pattern arising from interaction of a laser beam scattered from the specimen and an unscattered portion of the laser beam wherein the interference pattern includes a normalized interference pattern comprised of the interference pattern divided by a background form of interference pattern wherein the background form is selected from the group of a previously recorded background image form, a normalization constant form and a numerical model for a background illumination pattern form, and the normalized interference pattern comprised of a pattern selectively fitted to a prediction methodology of light scattering, thereby providing further characteristic information about the specimen for processing by the computer readable medium; and the set of instructions further including a scattering function which upon execution provides non-transitory convergent solution data descriptive of properties of the specimen, thereby enabling characterization of at least one of a mechanical property, an optical property, and a chemical property of the specimen.

21. The computer readable medium as defined in claim 20 wherein the set of instructions include a Lorenz-Mie methodology.

22. The computer readable medium as defined in claim 20 wherein the data characteristic of the specimen includes information on at least one of size of the specimen and complex refractive index of the specimen.

23. The computer readable medium as defined in claim 20 wherein the interference pattern includes information arising from a plurality of different light wavelengths in the laser beam.

* * * * *